United States Patent
Sergio et al.

(10) Patent No.: US 6,379,614 B1
(45) Date of Patent: Apr. 30, 2002

(54) APPARATUS AND METHOD FOR STERILIZING AN INSTRUMENT AT SUBSTANTIALLY ROOM TEMPERATURE

(75) Inventors: Roberto M. Sergio, Jenkintown; Winfield Wood, Jr., Gywnedd, both of PA (US); Peter O. Sildve, GlenEllyn, IL (US)

(73) Assignee: Sermed Industries Inc., Abington, PA (US)

( * ) Notice: Subject to any disclaimer, the term of this patent is extended or adjusted under 35 U.S.C. 154(b) by 0 days.

(21) Appl. No.: 09/425,261

(22) Filed: Oct. 22, 1999

Related U.S. Application Data

(60) Provisional application No. 60/105,115, filed on Oct. 22, 1998, provisional application No. 60/105,225, filed on Oct. 22, 1998, and provisional application No. 60/105,221, filed on Oct. 22, 1998.

(51) Int. Cl.[7] .................................................. A61L 2/00
(52) U.S. Cl. ............................. 422/28; 422/32; 422/33; 422/3; 422/109; 422/116; 422/292; 422/297; 422/300
(58) Field of Search .............................. 422/28, 32, 33, 422/3, 109, 116, 292, 297, 300

(56) References Cited

U.S. PATENT DOCUMENTS

| | | | |
|---|---|---|---|
| 4,752,444 A | 6/1988 | Bowen et al. | |
| 5,008,079 A | 4/1991 | Wutzler et al. | |
| 5,037,623 A | 8/1991 | Schneider et al. | |
| 5,077,008 A | 12/1991 | Kralovic et al. | |
| 5,225,160 A | 7/1993 | Sanford et al. | |
| 5,348,711 A | 9/1994 | Johnson et al. | |

FOREIGN PATENT DOCUMENTS

DE      3239549 A1     4/1984

*Primary Examiner*—Krisanne Thornton
(74) *Attorney, Agent, or Firm*—Akin, Gump, Strauss, Hauer & Feld, L.L.P.

(57) ABSTRACT

An apparatus for sterilizing an instrument having an exterior surface at substantially room temperature includes a chamber having an interior compartment for receiving and housing the instrument. The interior compartment is maintained at a predetermined compartment temperature while the instrument is being sterilized. The chamber is releasably engagable with a portion of the instrument to support the instrument within the interior compartment. A fluid injection mechanism is in fluid communication with the chamber for supplying fluid to the chamber and for maintaining the fluid at a predetermined fluid temperature while the instrument is being sterilized. The chamber includes at least one fluid outlet for directing a flow of fluid onto the exterior surface of the instrument. The chamber further includes at least another fluid outlet to direct the flow of fluid onto the portion of the instrument engaged by the chamber. A method of sterilizing an instrument having an exterior surface at substantially room temperature includes the steps of: securing the instrument inside of a chamber by removably engaging a portion of the instrument to the chamber; removing bio-burden from the instrument by exposing the instrument to at least one bio-burden removing fluid while maintaining the chamber and the at least one bio-burden removing fluid at about a first predetermined temperature; and sterilizing the instrument, including the portion of the instrument engaged by the chamber, by exposing the instrument to at least one sterilizing fluid while maintaining the chamber and the at least one sterilizing fluid at about a second predetermined temperature.

25 Claims, 7 Drawing Sheets

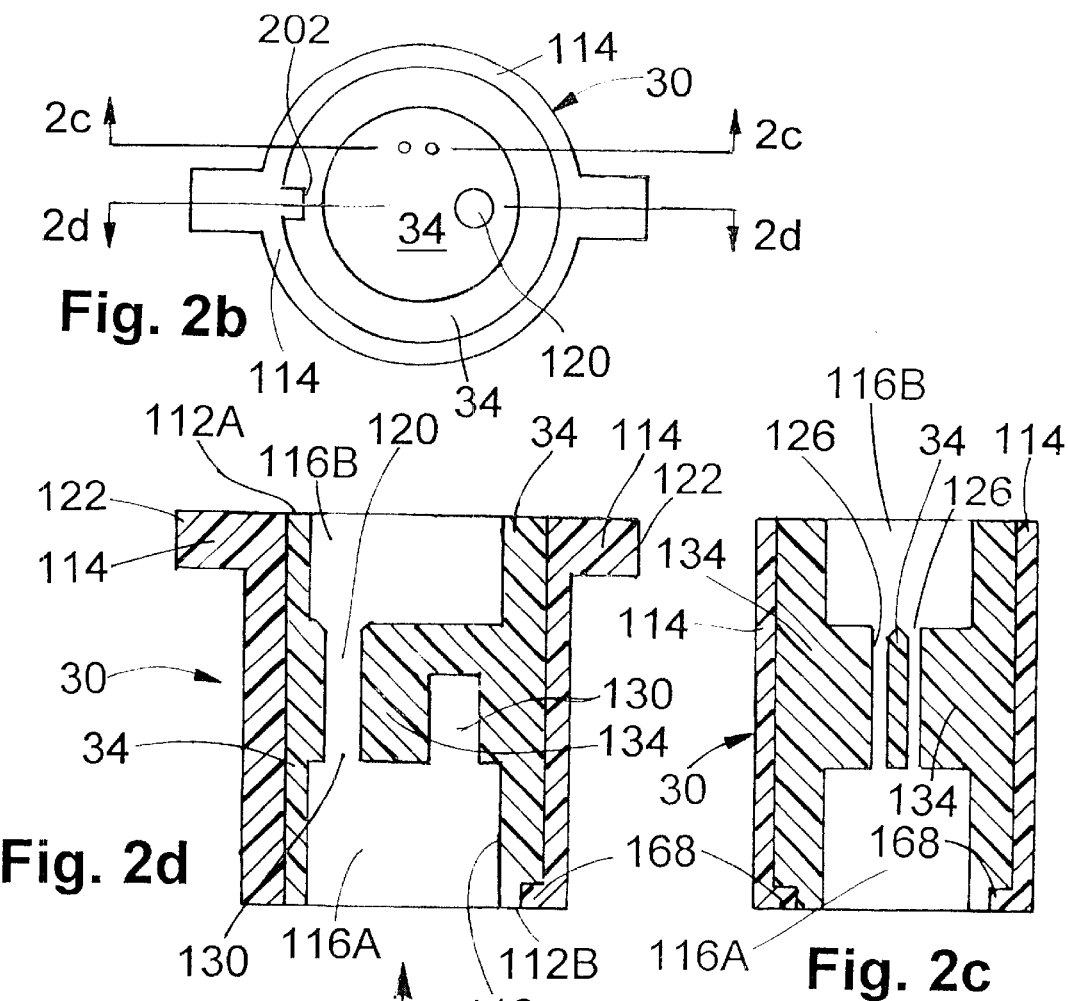
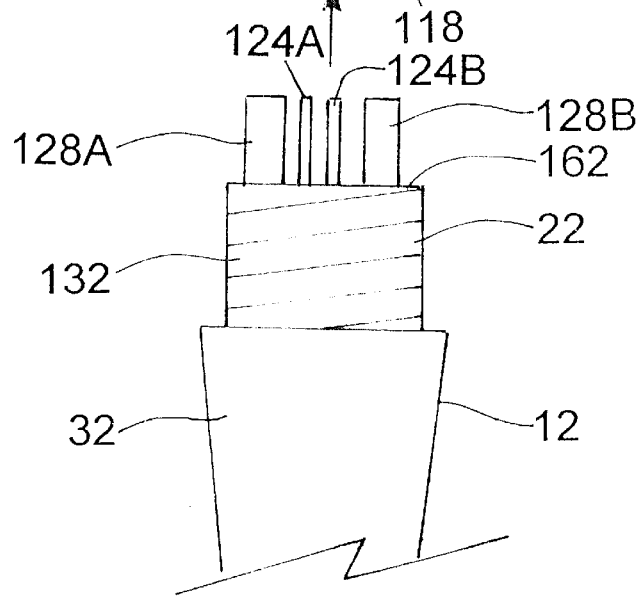

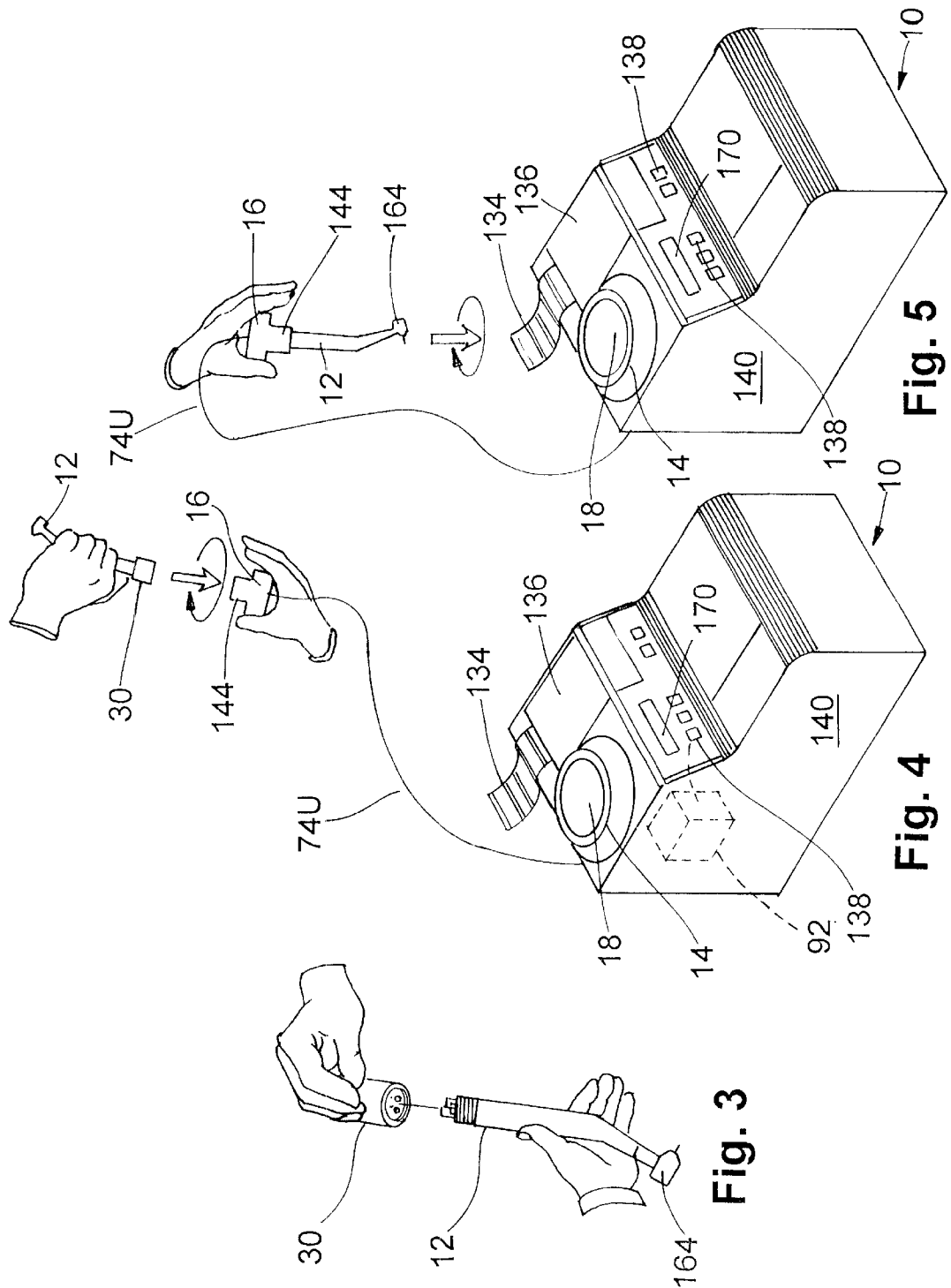

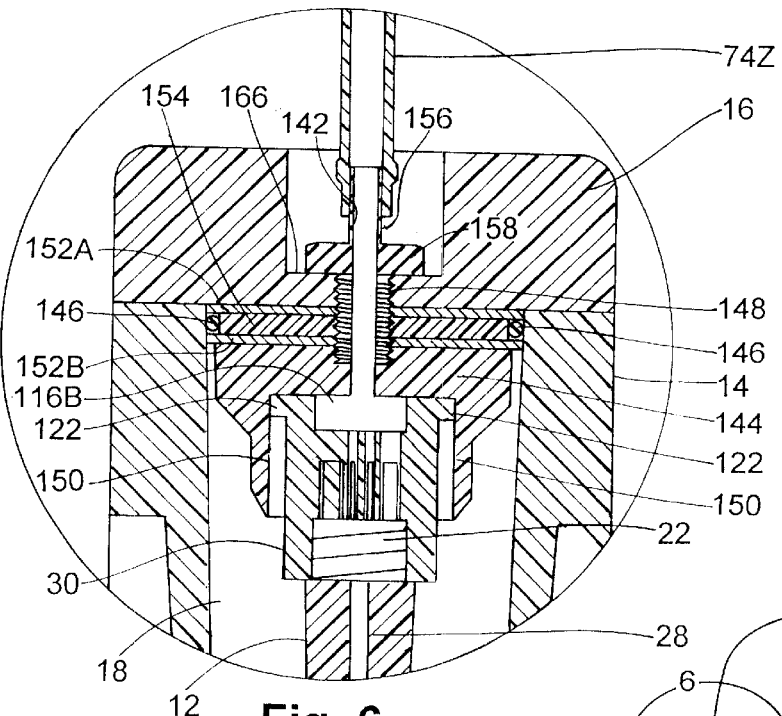
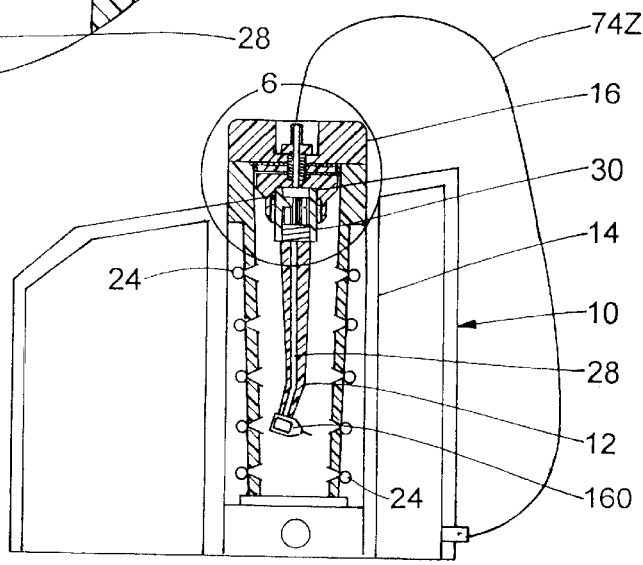

APPARATUS AND METHOD FOR STERILIZING AN INSTRUMENT AT SUBSTANTIALLY ROOM TEMPERATURE

CROSS-REFERENCE TO RELATED APPLICATIONS

This application claims priority from U.S. Provisional Patent Application No. 60/105,115 entitled, "Method and Apparatus for the Sterilization of Dental Handpieces at Room Temperature" filed Oct. 22, 1998, which is hereby incorporated by reference herein in its entirety. This application also claims priority from U.S. Provisional Patent Application No. 60/105,225 entitled, "Apparatus for the Sterilization of Threaded Areas of Dental Handpieces" filed Oct. 22, 1998, which is hereby incorporated by reference herein in its entirety. This application also claims priority from U.S. Provisional Patent Application No. 60/105,221 entitled, "Cartridge Assembly for Sterilant Containment" filed Oct. 22, 1998, and is hereby incorporated by reference herein in its entirety.

BACKGROUND OF THE INVENTION

The present invention relates to the sterilization of thermosensitive instruments and, more specifically, to an apparatus and a method for sterilizing thermosensitive instruments while exposing the instruments to substantially room temperatures during the sterilization process.

Current methods for sterilizing medical instruments include using steam autoclaves, using ethylene oxide, or using irradiation. While these methods are effective for sterilizing instruments, none of these methods are suitable for performing instrument sterilization at a patient side location while exposing the instrument to substantially room temperatures during the sterilization process.

Steam autoclaves operate at temperatures ranging between two hundred-forty degrees Fahrenheit and two hundred seventy-five degrees Fahrenheit for extended periods of time. The high temperatures used by steam autoclaves have been known to damage thermosensitive instruments, such as the turbines of a dental handpiece, and tend to reduce the useful life of the thermosensitive instruments that are sterilized using steam autoclaves. This results in the associated medical instruments requiring more frequent and expensive refurbishing.

Ethylene oxide is a carcinogenic, flammable, and highly toxic substance. Expensive ventilation systems are required before the discharge resulting from the ethylene oxide sterilization process is released to the atmosphere. Thus, the use of ethylene oxide raises safety issues with regard to the sterilization of instruments at a patient-side location. Problematic environmental issues are also associated with the use of ethylene oxide.

The use of irradiation for sterilization is not a practical solution for normal patient-side applications. Irradiation sterilization requires large and expensive installations and protective measures which makes irradiation sterilization unsuitable for use at a patient-side location.

Currently, the pre-cleaning of soiled medical instruments prior to the exposure of the instrument to the actual sterilizing heat, chemicals, or radiation depends on manual cleaning which is performed by medical personnel. The reliance on medical personnel for the manual cleaning of instruments increases the chance of inadequate cleaning due to human error or due to the omission of pre-cleaning all together.

What is needed, but so far not provided in the sterilizing art is an apparatus and method for sterilizing thermosensitive instruments at substantially room temperature, using automated processes, which does not require a manual pre-cleaning, in a manner that is convenient and safe for use at a patient-side location during the treatment of the patient.

SUMMARY OF THE INVENTION

Briefly stated, the present invention is directed to an apparatus for sterilizing an instrument having an exterior surface at substantially room temperature. The apparatus includes a chamber having an interior compartment for receiving and housing the instrument. The interior compartment is maintained at a predetermined compartment temperature while the instrument is being sterilized. The chamber is releasably engageable with a portion of the instrument to support the instrument within the interior compartment. A fluid injection mechanism is in fluid communication with the chamber for supplying fluid to the chamber and for maintaining the fluid at a predetermined fluid temperature while the instrument is being sterilized. The chamber includes at least one fluid outlet for directing a flow of fluid onto the exterior surface of the instrument. The chamber further includes at least another fluid outlet to direct the flow of fluid onto the portion of the instrument engaged by the chamber.

The present invention is alternatively directed to a method of sterilizing an instrument having an exterior surface at substantially room temperature. The method includes the steps of: securing the instrument inside of a chamber by removably engaging a portion of the instrument to the chamber; removing bio-burden from the instrument by exposing the instrument to at least one bio-burden removing fluid while maintaining the chamber and the at least one bio-burden removing fluid at about a first predetermined temperature; and sterilizing the instrument, including the portion of the instrument engaged by the chamber, by exposing the instrument to at least one sterilizing fluid while maintaining the chamber and the at least one sterilizing fluid at about a second predetermined temperature.

Alternatively, the present invention is directed to a coupler for supporting an instrument inside of a sterilizing apparatus. The coupler includes a porous body having a first end and a second end. The porous body receivably engages a portion of the instrument on the second end. A non-porous body substantially surrounds the porous body causing a flow of a fluid that enters the first end to flow toward the second end of the porous body and into contact with the portion of the instrument engaged by the coupler to expose the portion of the instrument to the fluid.

BRIEF DESCRIPTION OF THE SEVERAL VIEWS OF THE DRAWINGS

The foregoing summary, as well as the following detailed description of the preferred embodiment of the invention, will be better understood when read in conjunction with the appended drawings. For the purpose of illustrating the invention, there is shown in the drawings an embodiment, which is presently preferred. It is understood, however, that the invention is not limited to the precise arrangement and instrumentality shown. In the drawings:

FIG. 2a is an enlarged partial view of a proximal end of the instrument shown in FIG. 1;

FIG. 2b is an enlarged top planar view of a coupler of FIG. 1;

FIG. 2c is an enlarged cross-sectional view of the coupler of FIG. 2b as taken along the lines 2c—2c of FIG. 2b;

FIG. 2d is an enlarged cross-sectional view of the coupler of FIG. 2b as taken along the lines 2d—2d of FIG. 2b;

FIG. 3 is a perspective view of the instrument of FIG. 1 being attached to the coupler of FIGS. 2c and 2d;

FIG. 4 is a perspective view of the apparatus of FIG. 1 illustrating the insertion of the combination of the instrument and the coupler of FIG. 3 into a lid, which includes a coupler housing, of the apparatus of FIG. 1;

FIG. 5 is a perspective view showing the insertion of the instrument, which is attached to the lid of the chamber of FIG. 1, into the apparatus;

FIG. 6 is an enlarged cross-sectional view of a portion of the instrument after the instrument has been securely mounted in an interior compartment of the chamber of FIG. 1;

FIG. 7 is a cross-sectional view of the instrument mounted within the interior compartment of the chamber of FIG. 1;

DETAILED DESCRIPTION OF THE INVENTION

Figure 1:
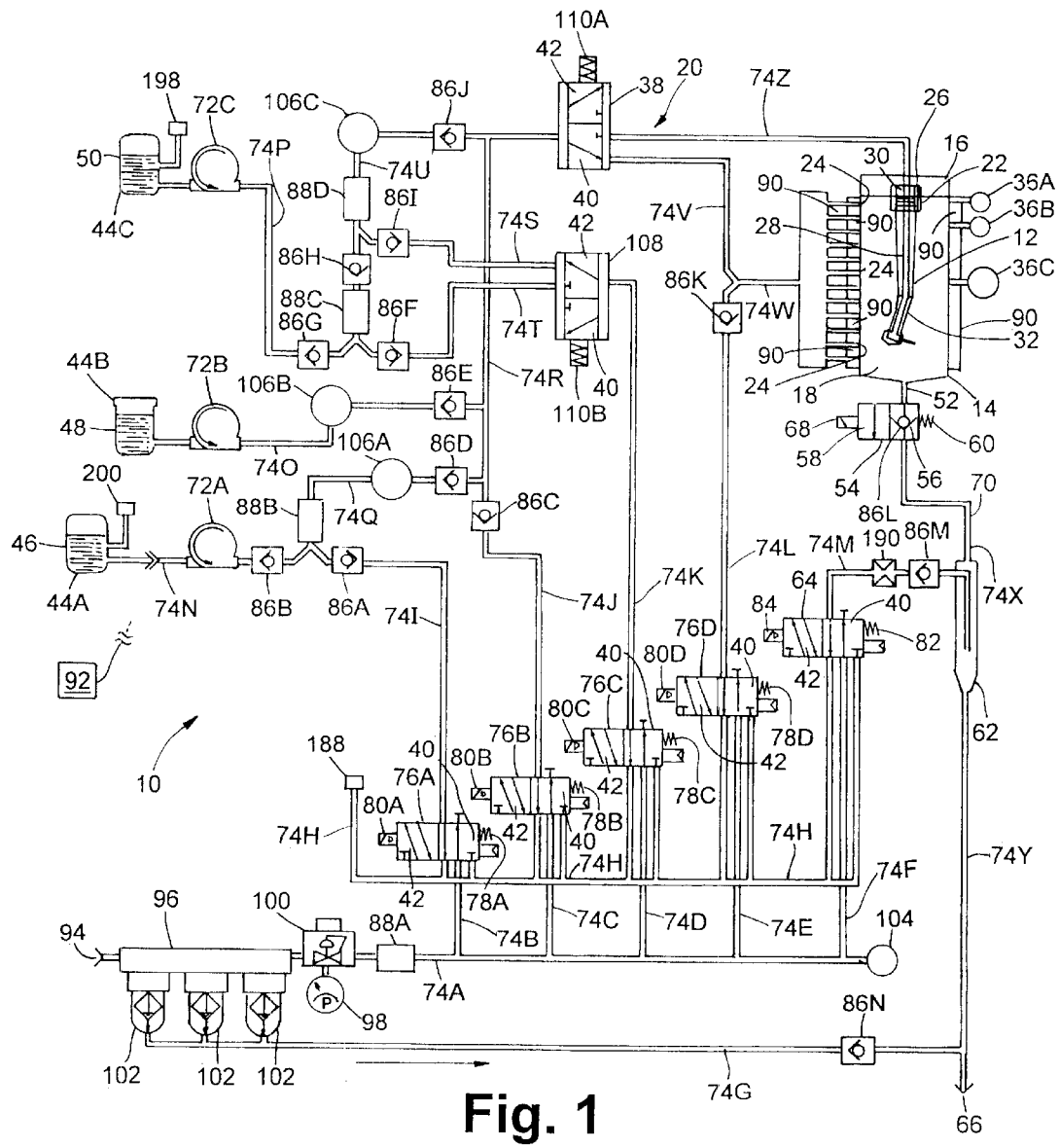
FIG. 1 is a schematic of an apparatus for sterilizing an instrument according to a preferred embodiment of the present invention.

Certain terminology is used in the following description for convenience only and is not limiting. The words "right," "left," "lower," and "upper" designate directions in the drawings to which reference is made. The words "inwardly" and "outwardly" refer to directions toward and away from, respectively, the geometric center of the sterilizing apparatus and designated parts thereof The terminology includes the words above specifically mentioned, derivatives thereof, and words of similar import. Additionally, the word "a," as used in the specification and in the claims, means "at least one."

Referring to the drawings in detail, wherein like numerals indicate like elements throughout, there is shown in FIGS. 1–10 a preferred embodiment of an apparatus, generally designated 10, for sterilizing an instrument at substantially room temperature. Briefly speaking, the present invention allows for an instrument 12 to be sterilized at a patient-side location during the treatment of a patient. The instrument 12, can be placed inside a chamber 14 where repeated operations are performed to clean and sterilize the instrument 12.

The preferred instrument 12 for use with the present invention is a dental handpiece. However, those of skill in the art will appreciate from this disclosure that instruments other than dental handpieces can be sterilized using the apparatus 10 and method of the present invention. For example, scalpels, forceps, prongs, tubes, tray, or any instrument used in a sterile lab, operating room, manufacturing site or the like can be sterilized in a quick and convenient manner using the apparatus 10 and the method of the present invention. Accordingly, while the preferred instrument 12 is discussed below as having an interior 28 (as is common in dental handpieces), those of skill in the art will appreciate from this disclosure that the present invention is not limited to instruments 12 having an interior 28. Thus, instruments such as a scalpel or the like can be used with the apparatus 10 or method of the present invention without departing from the scope of the invention.

Referring to FIG. 1, an apparatus 10 for sterilizing an instrument 12 at substantially room temperature is shown. The instrument 12 has an exterior surface 32 which has a proximal end 162 that is attachable to the chamber 14. When the apparatus 10 of the present invention is used with a dental handpiece, a distal end 164 of the instrument 12 houses a rotary turbine 160. Additionally, the dental handpiece 12 has a pair of lumens 124A, 124B, which extend from the proximal end 162 of the instrument 12. The first lumen 124A transports air and the second lumen 124B transports water to the distal end of the instrument 12. Air is injected into the handpiece 12 through the first large lumen 128A to turn the rotary turbine 160. Then, the air is exhausted through the second large lumen 128B. The first and second large lumens 128A, 128B each extend from the proximal end 162 of the instrument 12 to facilitate, in combination with a threaded portion 132 of the handpiece 12, the attachment of the dental handpiece 12 to a dental apparatus (not shown). Referring to FIG. 2a, a portion of the proximal end 162 of the dental handpiece preferably has threads 132 for securing the dental handpiece to the appropriate dental apparatus (not shown).

Referring to FIGS. 1, 4, and 5, the apparatus 10 includes a chamber 14 having an interior compartment 18 for receiving and housing the instrument 12. The chamber 14 is preferably generally cylindrically shaped. However, those of skill in the art will appreciate from this disclosure that the chamber 14 of the present invention is not limited to any particular shape. For example, the chamber 14 may be rectangularly shaped, triangularly shaped, cubically shaped or the like without departing from the scope of the present invention.

The chamber 14 includes a cover or lid 16, which is removably attachable to the chamber 14. Referring to FIG. 4, during the sterilization process the instrument 12 is attached the lid 16 via a coupler 30, further described below. Referring to FIGS. 4, 5, and 6, the lid 16 includes a coupler housing 144. The coupler housing 144 is attached on an inner surface of the lid 16 and projects into the interior compartment 18 of the chamber 14 when the lid 16 is positioned to seal the chamber 14.

Referring to FIGS. 6 and 7, the coupler housing 144 is secured to the lid 16 via a fastening member 148, which extends inwardly into the chamber 14 from a sleeve member 156. The sleeve member 156 is designed to engage a twenty-sixth conduit 74Z of a fluid injection mechanism 20, further described below, and forms a channel through the lid 16 of the chamber 14 to transfer fluids into the chamber 14. The sleeve member 156 is preferably tubular shaped and capable of slidably engaging the twenty-sixth conduit 74Z. The lower end of the sleeve member 156 forms a base 158 which abuts an outer surface of the lid 16. The fastening member 148 is preferably integrally formed with the base 158 of the sleeve member 156 which is positioned in a recess 166 in the outer surface of the lid 16. The lower end of the fastening member 148 extends through the lid 16 and into the coupler housing 144. Thus, the fastening member 148 braces the lid 16 between the coupler housing 144 and the base 158 of the sleeve member 156.

The conduits used with the apparatus 10 are preferably polyethylene and/or nylon and have an external diameter of about four millimeters and an internal diameter of about two and one half millimeters. However, those of ordinary skill in the art will appreciate from this disclosure that the particular materials and size of the conduits can be changed without departing from the scope of the present invention. For example, any type of conduits can be used that can withstand the pressures, temperatures, and fluids used with the apparatus 10 without departing from the scope of the present invention. Additionally, the size of the conduits can be adjusted depending on the flow rates and pressures which are used with the apparatus 10 without departing from the scope of the present invention.

First and second plates 152A, 152B are interposed between the lid 16 and the coupler housing 144. The first plate 152A is flush against the inner surface of the lid 16, and the second plate 152B is positioned a predetermined distance from the first plate 152A via a spacer 154. Around the spacer 154, is a seal, such as an O-ring, 146 which is used to form a seal between the interior compartment 18 of chamber 14 and the surroundings. The fastening member 148 extends downwardly from the base 158 of the sleeve member 156, through the lid 16, through the first and second plates 152a, 152b, through the spacer 154, and then securely engages the coupler housing 144. Referring to FIG. 6, clips 150 are preferably attached inside the coupler housing 144 and are generally positioned on the left and right sides of the coupler 30. The clips 150 secure the coupler 30 within the coupler housing 144 to facilitate the sterilization of the instrument 12. However, those of skill in the art will appreciate from the present disclosure that various other structures or methods can be used to secure the coupler 30 to the coupler housing 144 without departing from the scope of the present invention. For example, a friction fit, interlocking prongs, a latching member or the like can be used to secure the coupler 30 to the coupler housing 144.

The chamber 14 is preferably formed of polyethylene tetrachloride. However, those of skill in the art will appreciate that the chamber 14 may be formed of any material having suitably low absorption and high acid resistance such as, inconnel, stainless steel, composites, or the like.

While the lid 16 preferably includes the first and second plates 152A, 152B, the spacer 154, the seal 156, the coupler housing 144, and the fastening member 148, those of skill in the art will appreciate from this disclosure that the particular configuration used to attach the coupler 30 to the lid 16 is not critical to the present invention. One important aspect of the lid 16 is that the lid 16 is capable of receivably engaging and supporting the instrument 12 within the chamber 14.

The interior compartment 18 is preferably maintained at a predetermined compartment temperature while the instrument 12 is being sterilized. The chamber 14 is releasably engagable with a portion 22 of the instrument 12 to support the instrument 12 within the interior compartment 18. Referring to FIGS. 2a, 6, and 7, the portion 22 of the instrument 12 bears threads 132 which are used to attach the instrument 12 to an apparatus (not shown). Referring to FIGS. 2a, 2b, and 3, the instrument 12 is attached to the coupler 30 by inserting the instrument 12 into the coupler 30. Then, referring to FIG. 4, the coupler 30 and the associated instrument 12, is inserted into the coupler housing 144 of the lid 16.

The coupler 30 is removably attached to the interior compartment 18 and is engagable with the portion 22 of the instrument 12 to secure the instrument 12 within the chamber 14. Referring to FIGS. 2b and 3, the coupler 30 preferably, but not necessarily, has a cylindrical shape. Referring to FIGS. 6 and 7, the coupler 30 supports the instrument 12 inside of the sterilizing apparatus 10. The coupler preferably includes a porous body 34 having a first end 112A and a second end 112B. The porous body 34 receivably engages a portion 22 of the instrument 12 on the second end 112B.

Referring to FIGS. 2c and 2d, the porous body 34 has shaped notches, or recesses, 116A, 130, 126 which are designed to engage the particular instrument 12 being used with the apparatus 10. The configuration of the porous body 34 can be designed to generically fit multiple instruments 12 or it can be designed to specifically connect with a particular type of instrument 12. For example, the porous body 34 illustrated in FIGS. 2b, 2c, and 2d has specifically shaped recesses 116A, 126, 130 to facilitate the attachment of a dental handpiece, or any other instrument 12, to the coupler 30. The shape of the preferred porous body 34 is specifically designed for use with dental handpieces. However, those of ordinary skill in the art will appreciate from this disclosure that the porous body 34 can have other shapes to specifically engage other types of instruments 12. The second end 112B of the coupler 30 has a first recess 116A which includes large lumen receivers 130 that accommodate the large lumens 128A, 128B located on the proximal end 162 of the handpiece 12. Additionally, the first recess 116A also includes lumen receivers 126 for receiving the lumens 124A, 124B from the dental handpiece 12.

A non-porous body 114 substantially surrounds the porous body 34 to cause a flow of a fluid that enters the first end 112A to flow toward the second end 112B of the porous body 34 and into contact with the portion 22 of the instrument 12 that is engaged by the coupler 30 to expose the portion 22 of the instrument 12 to the fluid. The non-porous body is preferably formed of a polyethylene material. However, those of ordinary skill in the art will appreciate from this disclosure that any non-porous material having suitable anti-corrosion and low absorption properties can be used without departing from the scope of the present invention. In this manner the portion 22 of the instrument which is used to support the instrument 12 within the chamber 14, including the threads 132, lumens 124A, 124B, large lumens 128A, 128B etc. is exposed to the fluid as hereinafter described. The non-porous body 114 preferably has a circumferential lip 168 extending around the second end 112B of the coupler 30 and projecting radially inward. Referring to FIG. 2b, the non-porous body 114 has an inwardly projecting member 202 which forms a key for properly aligning the coupler 30 with the coupler housing 144. The projecting member 202 has a rectangular shape and extends along the entire longitudinal length of the inner surface of the non-porous body 114.

The porous body 34 also directs a flow of the fluid into the interior 28 of the instrument 12. The second end 112b of the coupler 30 preferably has a first recess 116A for receivably engaging the instrument 12. More specifically, the first recess 116A preferably uses a friction fit to engage the instrument 12. The friction fit is preferably partially due to the sponge-like qualities of the porous body 34 combined with the particular size of the lumens 124A, 124B and the large lumens 128A, 128B with the corresponding shape of the first recess 116A.

The coupler 30 preferably has a second recess 116B on a first end 112A for receiving the fluid. Referring to FIGS. 2c and 2d, the coupler 30 preferably, but not necessarily, includes at least one chute, or small lumens receivers, 126 and one large intake lumen receiver 130, which extends between the first recess 116A and the second recess 116B to direct the flow of the fluid into the interior 28 of the instrument 12. Thus, porous body 34 of the coupler 30 also directs a flow of the fluid via the right large exhaust lumen (which is blocked) 12 onto the portion 22 of the instrument 12 engaged by the coupler 30. The coupler 30 preferably directs a flow of the fluid into any interior 28 of the instrument 12 that has a fluid pathway connection to the portion 22 of the instrument 12 engaged by the chamber 14.

Referring to FIGS. 2b and 2d, the coupler 30 includes a pair of prongs 122 extending outwardly from the non-porous body 114. The porous body 34 can be a separate piece that allows the portion 22 of the instrument 12 to be threadably engaged therein. A removable porous body 34 can be located at the at the distal end of the coupler 30 (i.e., the end of the coupler 30 closest to the handpiece 12) for ease of attachment.

Referring to FIG. 1, the chamber 14 preferably includes a first sensor 36A for detecting when the chamber 14 is closed. The first sensor 36A is preferably a non-contact magnetic proximity sensor of the well known in the art. However, those of skill in the art will appreciate from this disclosure that any sensor capable of determining when the lid 16 is secured to the chamber 14 can be used without departing from the scope of the present invention. A second sensor 36B detects when the instrument 12 is positioned within the interior compartment 18. The second sensor 36B is preferably an infrared sensor. However, those of skill in the art will appreciate from this disclosure that any sensor capable of detecting when the instrument 12 is positioned within the interior compartment 18 without interfering with the sterilization process can be used. A third sensor 36C detects a temperature of the interior compartment 18. The third sensor is preferably a thermocouple. However, those of ordinary skill in the art will appreciate from this disclosure that any sensor capable of detecting the compartment temperature can be used without departing from the present invention.

A controller 92 is operatively engaged with the chamber 14, a fluid injection mechanism (further detailed below) 20, the first sensor 36A, the second sensor 36B, and the third sensor 36C for regulating the flow of the fluid through the apparatus 10. The controller 92 preferably uses an ATMEL 89C52 processor. However, those of ordinary skill in the art will appreciate from this disclosure that any suitable imbedded microprocessor assembly can be used to control and monitor the apparatus 10 without departing from the scope of the present invention. The processor is preferably attached to a customized control board having customized hardware interface electronics that are adapted for use with the sterilizing apparatus 10.

A specially designed software program activates all the processes and monitors, in real time, the accuracy of the steps used to sterilize the instrument 12. Referring to FIGS. 4 and 5, a liquid crystal display 170 is preferably used to monitor the functions of the apparatus 10 while a printer 136 preferably prints out an operational log 134 detailing the various operations of the apparatus 10.

Figure 10:
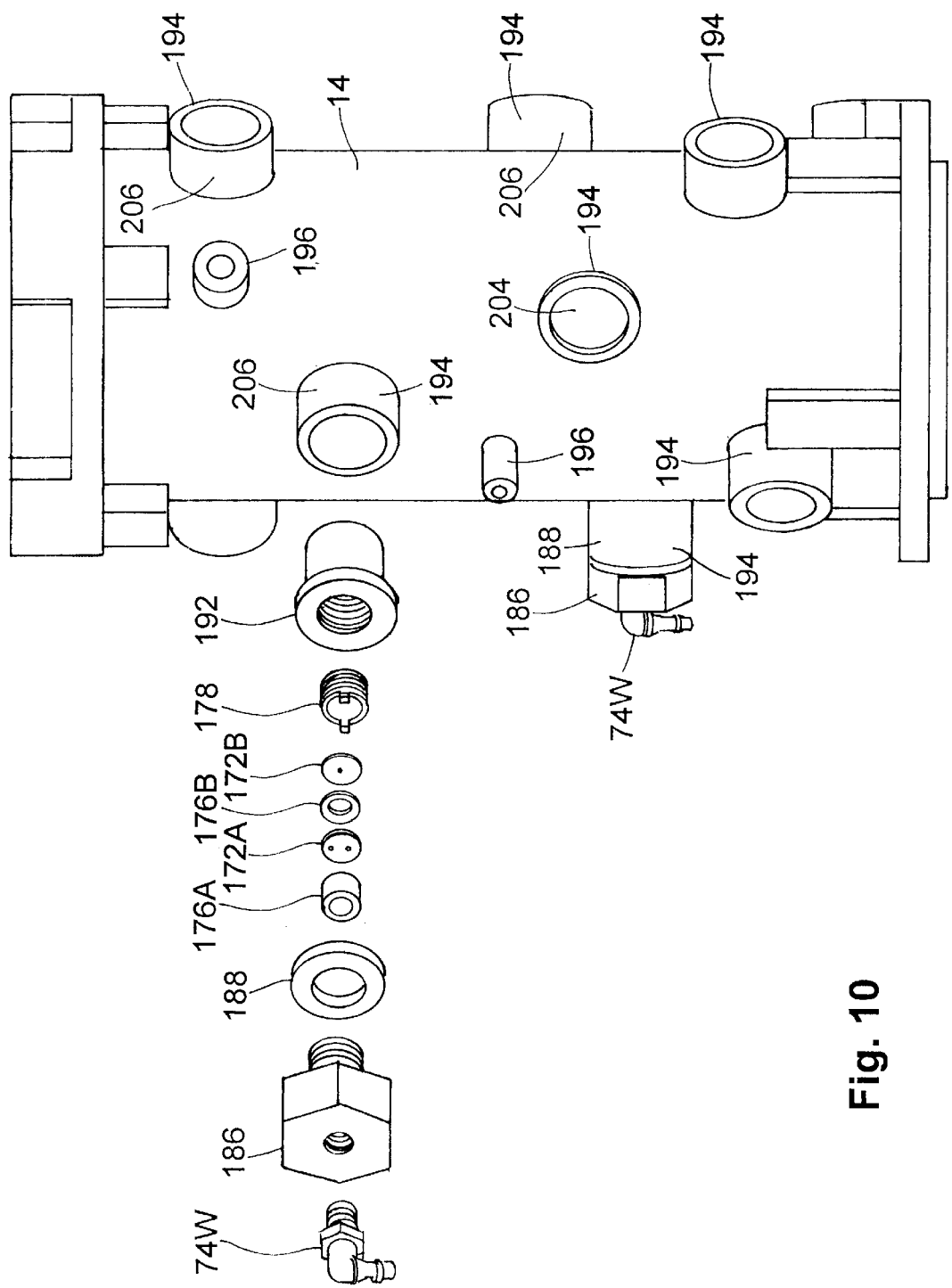
FIG. 10 is a perspective view of the exploded nozzle of FIG. 9 aligned for insertion into the chamber of FIG. 1.

Referring to FIG. 10, the chamber 14 preferably has multiple nozzle receivers 194. Each nozzle receiver 194 preferably includes a tubular projection 206 which extends outwardly from the outer surface of the chamber 14. The tubular projections 206 enclose a chute 204 that extends through the tubular projection 206 and through the wall of the chamber 14. The chute 204 allows a nozzle (further detailed below) 24 to be secured therein. Two sensor receivers 196 are shown on the chamber 14. The sensor receiver 196 closer to the top of the chamber is preferably designed for use with the second sensor 36B which is used to determine whether an instrument 12 is positioned within the chamber 14. The sensor receiver 196 that is positioned closer to the bottom of the chamber 14 is preferably designed for use with the third sensor 36C which detects the temperature of the interior compartment 18.

While a preferred embodiment of the chamber has been described in detail above, those of skill in the art will appreciate from this disclosure that various structural features of the chamber 14 can be altered without departing from the scope of the present invention. For example, the particular connections between the instrument 12 and the chamber 14 may be varied as long as proper sterilization of the instrument 12 is not affected.

The fluid injection mechanism 20 is in fluid communication with the chamber 14 for supplying fluid to the chamber 14 and for maintaining the fluid at a predetermined fluid temperature while the instrument 12 is being sterilized. The fluid injection mechanism 20 uses a combination of fluid pumps (further detailed below) 72A–72C and pressurized air to transport appropriate fluids, further detailed below, through the chamber 14 for the cleaning and sterilizing of the instrument 12. The fluid is delivered by the fluid injection mechanism 20 to the chamber using either the twenty-sixth conduit 74Z or using a twenty-third conduit 74W.

The predetermined compartment temperature and the predetermined fluid temperature are preferably maintained within the range of between about fifty-five degrees Fahrenheit and about ninety-five degrees Fahrenheit during the sterilization of the instrument 12. This allows the instrument 12 to be sterilized while only being exposed to substantially room temperatures and thus prevents damage to thermosensitive instruments 12, such as dental handpieces. The currently preferred predetermined compartment temperature and the currently preferred predetermined fluid temperature are within the range of between about ninety degrees Fahrenheit and about ninety-four degrees Fahrenheit during the sterilization of the instrument 12. While preferred ranges have been detailed above, those of skill in the art will appreciate from this disclosure that the preferred temperature ranges assume an exposure of the instrument 12 to a sterilizing fluid 50 comprising a peracetic acid, further detailed below, for a time period between about three minutes and about six minutes. Additionally, the above temperature ranges are preferred for an apparatus 10 that completes the sterilization process, further detailed below, within a time period between of about ten minutes and about twelve minutes. Those of skill in the art will appreciate from this disclosure that if the time periods for completion of the sterilization process, or the associated exposure of the instrument to the sterilizing liquid were increased, or if a different type of sterilizing fluid were used with the apparatus then temperatures other than those detailed above could be used in combination with the apparatus 10 without departing from the scope of the present invention.

The fluid used by the apparatus 10 is any one of a rinse fluid 46, a bio-burden removal fluid 48, a sterilizing fluid 50, and filtered air. The rinse fluid 46 preferably comprises sterilized water. However, those of skill in the art will appreciate from this disclosure that any suitably sterile fluid capable of rinsing the instrument 12, which is safe for exposure to and consumption by patients can be used as the rinse fluid 46. The bio-burden removal fluid 48 preferably comprises a protease fluid. However, those of skill in the art will appreciate from this disclosure that any fluid capable of safely removing bio-burden from a soiled instrument 12 to simplify the killing of pathogen can be used as the bio-burden removal fluid 48. The sterilizing fluid 50 preferably comprises a peracetic acid. However, those of skill in the art will appreciate that the sterilizing fluid 50 may contain any components, which contribute to the killing of pathogens and are safe for use at a patient-side location.

The chamber 14 includes at least one fluid outlet 24 for directing a flow of the fluid onto the exterior surface 32 of the instrument 12. Referring to FIGS. 1 and 7, twelve spaced fluid outlets 24 are preferably used in the chamber 14. However, those of skill in the art will appreciate from this disclosure that any number of fluid outlets 24 may be used to direct fluid onto the exterior surface 32 of the instrument 12 as long as proper amounts of the fluid can be directed onto the exterior surface 32 of the instrument 12. When the fluid injection mechanism 20 sends fluid to the fluid outlets 24, fluid is transported along the twenty-second conduit 74V to a twenty-third conduit 74W which guides the fluid into each of the fluid outlets 24.

Figure 8:
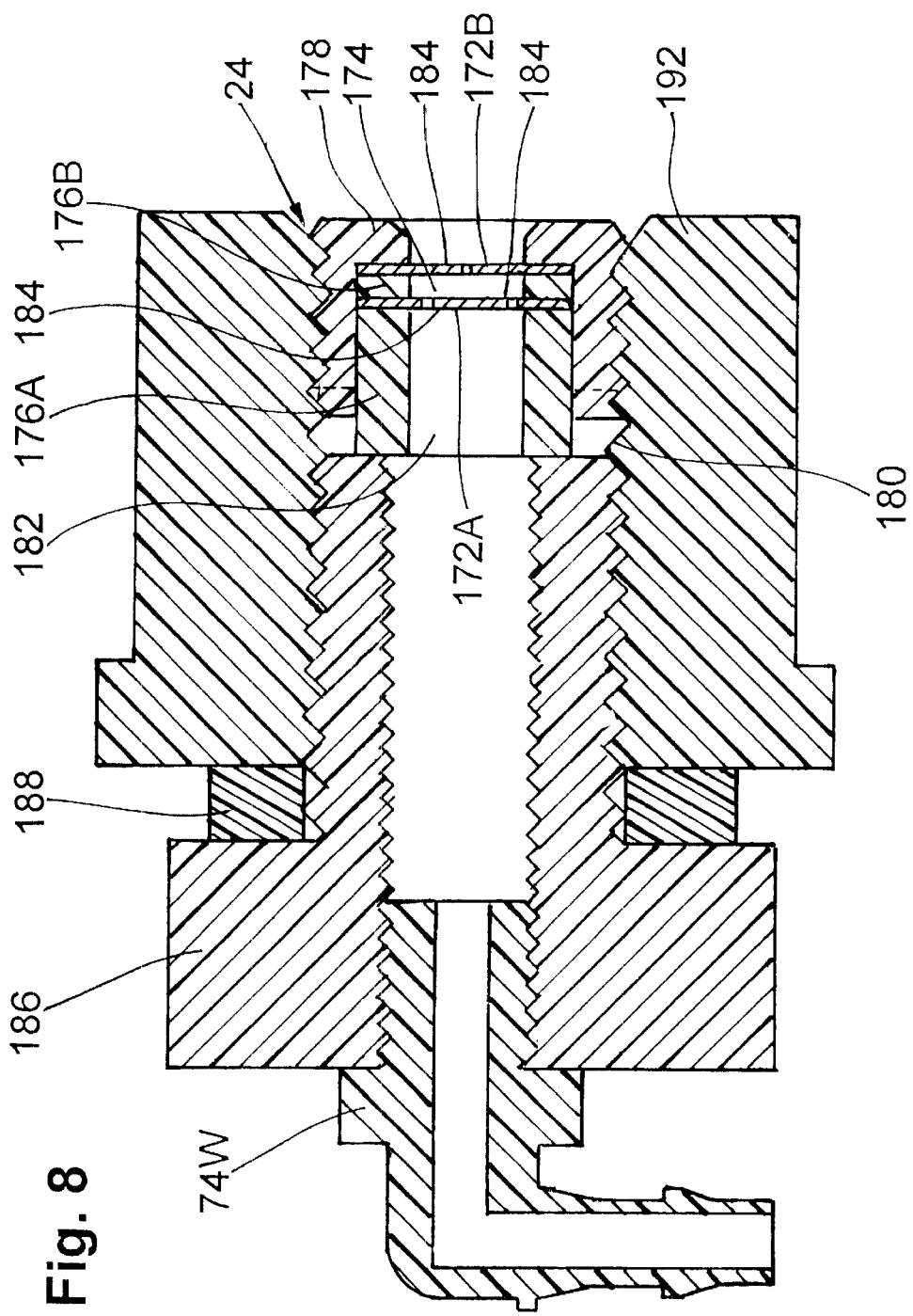
FIG. 8 is a cross-sectional view of a nozzle, which is not mounted into the chamber of FIG. 1.
Figure 9:
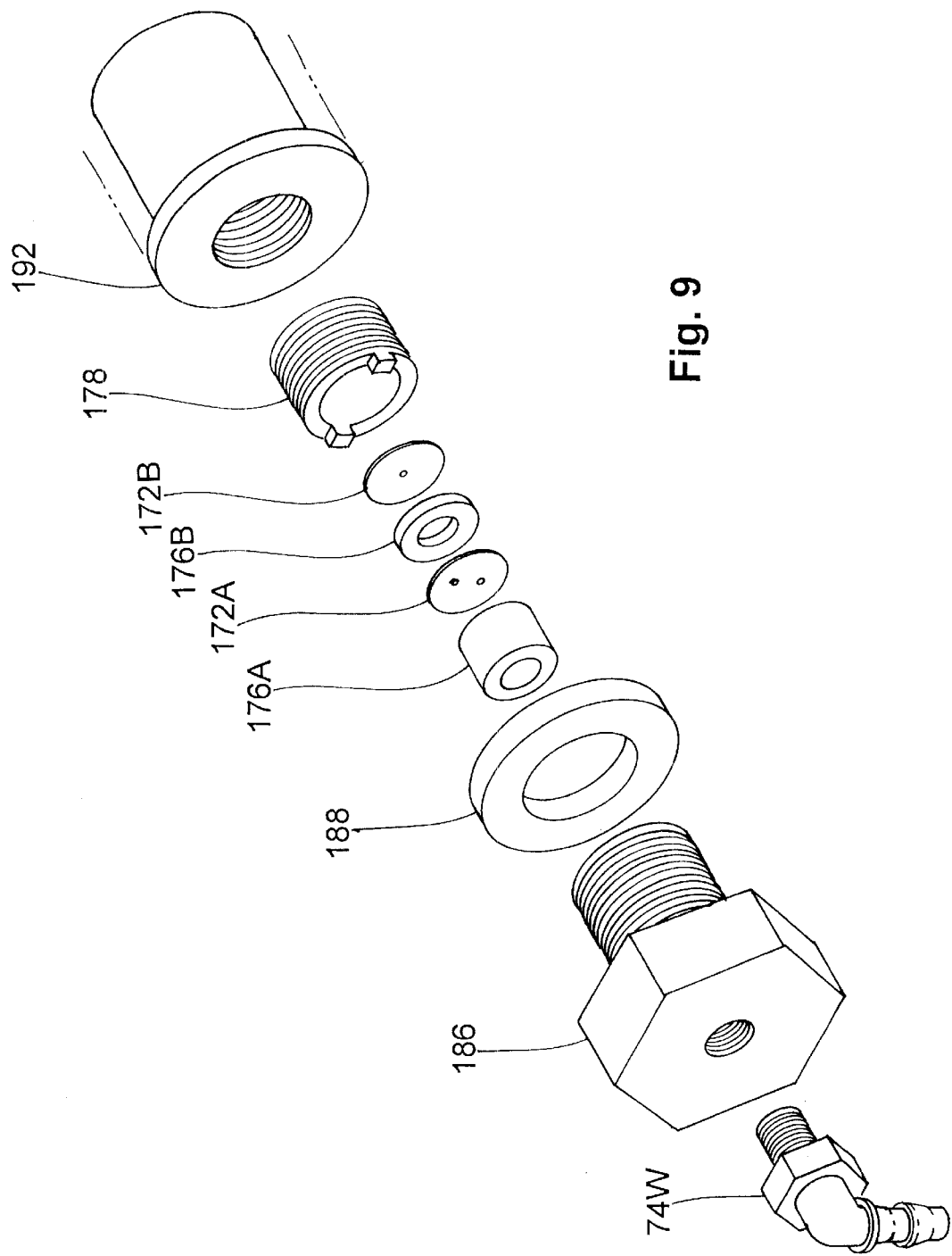
FIG. 9 is an exploded perspective view of the nozzle of FIG. 8.

The at least one fluid outlet 24 preferably, but not necessarily, comprises at least one nozzle 24 mounted to the chamber 14 to direct the flow of the fluid onto the exterior surface 32 of the instrument 12. Referring to FIGS. 8–10, each nozzle 24 is preferably inserted in the inner surface of the chamber 14. The spraying action of the nozzle is preferably caused by first and second nozzle plates 172A, 172B. The nozzle plates 172A, 172B are preferably disposed in a spaced apart parallel planar fashion to create a compartment 174 therebetween where turbulent fluid flow takes place as further detailed below. The nozzle 24 preferably includes a first and second generally annular spacer 176A, 176B, which are used to hold the first and second nozzle plates 172A, 172B in a spaced apart generally parallel planar fashion.

The first and second spacers 176A, 176B are preferably formed of a low absorption and non-reactive material such as nylon or the like. The first spacer 176A receives a fluid from the fluid injection mechanism 20, further detailed below. The first nozzle plate 172A has a first and second surface. The first surface is disposed on a distal end of the first spacer 176A and has at least one, but preferably two holes 184 extending therethrough. The second spacer 176B is disposed on the second surface of the first nozzle plate 172A and the second nozzle plate 172B is attached on an opposite end of the second spacer 176B from the first nozzle plate 172A and has a hole 184 therein. The first and second nozzle plates 172A, 172B and the first and second spacers 176A, 176B are held in position by a nozzle retainer 178. The nozzle retainer 178 is preferably circularly shaped to facilitate the threaded engagement between the nozzle retainer 178 and the threaded bore 180 which is disposed in a nozzle insert 192. It is preferable that the first and second nylon spacers 176A, 176B and the first and second nozzle plates 172A, 172B are circularly shaped. However, those of skill in the art will appreciate from this disclosure that the first and second nylon spacers 176A, 176B and the first and second nozzle plates 172A, 172B may have other shapes when viewed along the longitudinal axis of the nozzle 24 without departing from the scope of the present invention.

Referring to FIGS. 8-10, the first nozzle plate 172A is, positioned on the right side of the first nylon spacer 176A to form a chamber 182. The second nylon spacer 176B is positioned on the opposite side of the first nozzle plate 172A from the first nylon spacer 176A. The second nozzle plate 172B is positioned on the right side of the second nylon spacer 176B to form the compartment 174.

The first nozzle plate 172A has two holes 184 which allow fluid to pass from the chamber 182 into the compartment 174. A single hole 184 is preferably positioned in the second nozzle plate 172B. The combination of the positioning of the two holes 184 in the first nozzle plate 172A and the positioning of the one hole 184 in the second nozzle plate 172B combine to generate a turbulent fluid flow within the compartment 174 which results in the emission of a vigorous spray of the fluid from the hole 184 in the second nozzle plate 172B. The turbulent fluid flow in compartment 174 results in the spray having a shape similar to a cone with an angular width of about ninety degrees as measured from the hole 184 in the second nozzle plate 172B.

The first and second nozzle plates 172A, 172B and the nozzle retainer 178 are preferably formed of inconnel but may be formed of any low absorption corrosion resistant material capable of withstanding the fluid pressures used by the apparatus 10 such as other types of stainless steel or composites or the like. Engaged with the side of the nozzle 24 opposite from the interior compartment 18 of the chamber 14 is a conduit-securing bolt 186. The conduit securing bolt 186 is threadably inserted into the bore 180 in the nozzle insert 192 to form a fluid passageway between the twenty-third conduit 74W of the fluid injection mechanism 20 and the chamber 182 of the nozzle 24. A seal, such as an O-ring, 188 is preferably positioned between the flange of the conduit securing bolt 186 and the exterior surface of the nozzle insert 192.

Referring to FIG. 1, the fluid injection mechanism 20 includes reservoirs 44A, 44B, or 44C for storing the fluid and conduits extending between the reservoirs 44A–44C and the chamber 14. Pumps 72A, 72B, or 72C remove fluid from the reservoirs 44A, 44B, or 44C and drive the fluid through the conduits toward the chamber 14. The first and second pumps 72A, 72B which are used with the rinse fluid 46 and the bio-burden removing fluid 48 are preferably liquid diaphragm pumps. The third pump 72C which is used with the sterilizing fluid 50 is preferably a modified liquid diaphragm pump. More specifically, the third pump 72C is preferably a liquid diaphragm pump that has been modified to also act as a metering pump. The modified third pump 72C permits improved control over the amount of sterilizing fluid 50 which is used by the apparatus 10.

Additionally, the fluid injection mechanism 20 includes air valves 76A, 76B, 76C, or 76D for supplying pressurized air to remove fluid from the conduits and propel the fluid toward the chamber 14. The fluid injection mechanism 20 further includes heaters 88A–88D, 90 to maintain the fluid at approximately the predetermined fluid temperature.

The first through fourth heaters are preferably part of an independent thermal control circuit. Each heater preferably, but not necessarily, comprises a heating element, such as copper or the like, which is wrapped around the heater chamber and sealed with a jacket that covers the heating element. A thermocouple is preferably combined with the heaters 88A–88B to allow for the detection of the temperature of the fluid contained therein. Each thermal control circuit monitors the temperature of the associated fluid and automatically powers the heater 88A,–88D as necessary to bring the fluid substantially to the predetermined fluid temperature. Accordingly, each thermal control circuit preferably controls a respective heater so that all the controller 92 needs to monitor is the temperature of the fluid. Assuming the temperature of the fluid is within the predetermined range, the controller 92 will operate the rest of the liquid injection mechanism as further detailed below.

More specifically, the rinse fluid 46 is preferably contained within a first reservoir 44A, the bio-burden removal fluid 48 is preferably contained within a second reservoir 44B, and the sterilizing fluid 50 is preferably contained within a third reservoir 44C. Each of the reservoirs 44A–44C has an associated pump 72A–72C, which initially transports the fluid toward the chamber 14.

A heater is preferably not used to heat the bio-burden removing fluid 48 because the bio-burden removing fluid 48 is substantially brought to the predetermined fluid temperature due to the heat generated by the rinse fluid 46, the sterilizing fluid 50, the pressurized air, and the heater 90 which maintains the chamber 14 at the predetermined compartment temperature. Due to the relatively higher mass of the instrument 12 and the chamber 14, the bio-burden removing fluid 48 is heated to the predetermined fluid temperature without significantly altering the temperature of the instrument 12 or the chamber 14. Those of skill in the art will appreciate from this disclosure that a heater for the bio-burden removing fluid can be incorporated with the apparatus 10 without departing from the scope of the present invention.

Pressurized atmospheric air preferably enters the apparatus 10 via an inlet 94, which is attached to an air filter 96. The pressurized air is preferably supplied by a compressor (not shown) which is external to the apparatus 10. However, those of ordinary skill in the art will appreciate from this disclosure that a compressor could be incorporated with the apparatus 10 without departing from the scope of the present invention. The apparatus preferably uses about one cubic foot of air per minute at about seventy five pounds per square inch. However, those of ordinary skill in the art will appreciate from this disclosure that the amount of pressurized air that is used by the apparatus 10 can be modified depending on the size of the apparatus 10 and depending on the flow rates that the apparatus is designed to use without departing from the scope of the present invention.

The air filter 96 filters and guides the pressurized air to a pressure regulator 100, which is monitored via a pressure gauge 98. The pressure of the pressurized air is preferably in the range of between about 75 pounds per square inch and about 85 pounds per square inch. However, those of skill in the art will appreciate from this disclosure that the pressure of the pressurized air can be varied depending upon the specific components used to form the apparatus 10.

In the event of excessive pressure in the air filter 96, automatic discharge valves 102 open and cause air to be dumped from the apparatus via a seventh conduit 74G, through a fourteenth checkvalve 86N, and out through the apparatus outlet 66. Once the filtered air is transported past the pressure regulator 100, the pressurized air is heated using a first heater 88A and is then transported along a first conduit 74A. The pressure of the filtered air in the first conduit 74A is monitored by an inlet air pressure sensor 104. The inlet air pressure sensor 104 is preferably an electronic transducer. However, those of skill in the art will appreciate that any sensor capable of reliably monitoring the inlet air pressure can be used without departing from the scope of the present invention. The first conduit 74A supplies air to first through fourth air valves 76A–76D and a drain air valve 64 via second through sixth conduits 74B–74F respectively.

The checkvalves of the present invention are preferably acid resistant and relatively small sized. For example, the checkvalves of the present invention are preferably one half inch in length and one half inch in diameter. The checkvalves are preferably designed to interface with conduits that have an external diameter of about four millimeters.

Each of the first through fourth air valves 76A–76D and the drain air valve 64 are connected via an eighth conduit 74H to an air exhaust valve 188. Each of the air valves 76A–76D is shown in the first, or disengaged, position 40. While the first through fourth air valves 76A–76D, and the drain air valve 64 are in the first position 40, the exhaust valve 188 prevents pressurized air from remaining in the conduits connecting the respective air valves to the portion of the fluid injection mechanism 20 which transports the fluids, further detailed below. The first through fourth air valves 76A–76D and the drain air valve 64 are preferably SMC ™ air valves. The air valves are compact and measure about a half inch in length and have a half inch diameter. Each air valve preferably has a power consumption of about one half a Watt.

Referring to the first air valve 76A, the first air valve 76A is biased into the first position 40 via a first input biasing element 78A. When the first air valve 76A is in the first position 40, any pressurized air in a ninth conduit 74I is diverted through the eighth conduit 74H to the exhaust valve 188. A switch 80A is capable of moving the first air valve 76A from the first position 40 into the second position 42 which causes the filtered pressurized air that is supplied via the second conduit 74B to be applied to the ninth conduit 74I and through a first checkvalve 86A.

Referring to the second air valve 76B, the second air valve 76B is biased into the first position 40 by a second input biasing element 78B. While the second air valve 76B is in the first position 40, any pressurized air in a tenth conduit 74J is diverted to the exhaust valve 188 via the eighth conduit 74H. A second switch 80B can move the second air valve 76B into the second position 42 which causes filtered, pressurized air in the third conduit 74C to be applied to the tenth conduit 74J and driven through a third checkvalve 86C into the eighteenth conduit 74R.

Referring to the third air valve 76C, the third air valve 76C is biased into the first position 40 by a third input biasing element 78C. While the third air valve 76C is in the first position 40, any pressurized air in an eleventh conduit 74K is diverted to the exhaust valve 188 via the eighth conduit 74H. A third switch 80C can move the third air valve 76C into the second position 42. When the third air valve 76C is in the second position 42, filtered pressurized air from the fourth conduit 74D is provided to the eleventh conduit 74K. When pressurized air is driven into the eleventh conduit 74K, the air is guided to an air diverter valve 108.

The air diverter valve 108 has a second diverter switch 110B capable of moving the air diverter valve 108 between a first position 40 and a second position 42. The air diverter valve 108 is shown in the second position 42 in FIG. 1. While the air diverter valve 108 is in the second position 42, air from the eleventh conduit 74K is provided to a nineteenth conduit 74S and driven through a ninth checkvalve 86I. When the air diverter valve 108 is in the first position 40, pressurized air from the eleventh conduit 74K is provided to a twentieth conduit 74T and driven through a sixth checkvalve 86F. The operation and positioning of the air diverter valve 108 is further discussed below.

Referring to the fourth air valve 76D, a fourth input biasing element 78D biases the fourth air valve 76D into the first position 40. While the fourth air valve 76D is in the first position 40, any pressurized air in twelfth conduit 74L is diverted to the exhaust valve 188 via the eighth conduit 74H. A fourth switch 80D is capable of moving the fourth air valve 76D into the second position 42. While the fourth air valve 76D is in the second position 42, filtered pressurized air from the fifth conduit 74E is provided to the twelfth conduit 74L and driven through an eleventh checkvalve 86K.

Referring to the drain air valve 64, the drain air valve 64 is biased into a first position 40 by a drain-biasing element 82. While the drain air valve 64 is in the first position 40, pressurized air in a thirteenth conduit 74M is diverted to the exhaust valve 188 via the eighth conduit 74H. A drain switch 84 is capable of moving the drain air valve 64 into the second position 42. While the drain air valve 64 is in the second position 42, pressurized air from a sixth conduit 74F is provided to the thirteenth conduit 74M and driven through a restrictor 190 and a thirteenth checkvalve 86M. The restrictor 190 reduces the flow of the filtered pressurized air through the thirteenth checkvalve 86M. The restrictor 190 is preferably used because the flow of the pressurized air from the drain air valve 64 is in excess of that which is desired to create a suction effect to remove fluid from the chamber, as further detailed below.

Each of the first through fourth switches 80A–80D and the drain switch 84 are preferably integral with the SMC™, or similar type, air valve and are air assisted switches. In other words the switches are moved partially using electric power and then, are moved the rest of the way using a portion of the pressurized air. However, those of ordinary skill in the art will appreciate from this disclosure that the first through fourth switches 80A–80D may be separate components from their respective air valves without departing from the scope of the present invention. For example, electrically operated solenoid switches that are controlled by the controller 92. However, those of ordinary skill in the art will appreciate from this disclosure that any type of switch used for the positioning of valves can be used without departing from the scope of the present invention.

Rinse fluid 46 is removed from the first reservoir 44A and driven through a fourteenth conduit 74N by the first pump 72A. During one complete sterilization operation of the apparatus 10 about fifty millimeters to about one hundred fifty milliliters of rinse fluid 46 is preferably used. However, those of ordinary skill in the art will appreciate from this disclosure that depending on the size of the apparatus 10 and depending upon the type of rinse fluid 46 used, the amount of rinse fluid 46 that is processed by the apparatus 10 during one complete sterilization operation can be varied without departing from the scope of the present invention. An exhaust valve 200 is attached to the first reservoir 44A to allow air to enter the first reservoir 44A and to reduce the amount of force that must be generated by the first pump 44A to remove the rinse fluid 46 from the first reservoir 44A. The rinse fluid 46 is then driven through a second checkvalve 86B to the second heater 88B. The second heater 88B ensures that the rinse fluid 46 is at the predetermined fluid temperature prior to the controller 92 applying the rinse fluid 46 to the instrument 12 contained within the chamber 14, further detailed below. To apply the rinse fluid 46 to the instrument 12 contained within the chamber 14, the first pump 72A in combination with the first, second, and fourth air valves 76A, 76B, and 76D drives the rinse fluid 46 into the chamber 14 as described below.

To transfer the rinse fluid 46 from the second heater 88B to the chamber 14, the first air valve 76A is moved into the second position 42 to provide pressurized air to the ninth conduit 74I. When pressurized air is transferred through the ninth conduit 74I, the pressurized air passes the first checkvalve 86A to push heated fluid from the second heater 88B into a seventeenth conduit 74Q which guides the rinse fluid 46 to the first fluid sensor 106A. Then, the rinse fluid 46 is driven the past the fourth checkvalve 86D and into the eighteenth conduit 74R.

The second air valve 76B is then moved into the second position 42 to transfer pressurized air into the tenth conduit 74J, past the third checkvalve 86C, and into the eighteenth conduit 74R to push the rinse fluid 46 toward a diverter valve 38. The diverter valve 38 guides the rinse fluid 46 (or either one of the bio-burden removing fluid 48 and the sterilizing fluid 50, as appropriate) toward either the portion 22 of the instrument 12 that is engaged by the chamber 14 or toward the fluid outlets 24 disposed in the walls of the chamber 14. When the diverter valve 38 is in the first position 40; the rinse fluid is transferred to the twenty-second conduit 74V and into the twenty-third conduit 74W. Then, the fourth air valve 76D is moved into the second position 42 to transfer pressurized air from the fifth conduit 74E to the twelfth conduit 74L and then through the eleventh checkvalve 86K. The pressurized air that is driven through the eleventh check valve 86K aids in driving the rinse fluid 46 contained in the twenty-third conduit 74W into the fluid outlets 24 for application onto the exterior 32 of the instrument 12 contained within the chamber 14.

Alternatively, when the diverter valve 38 is in the second position 42, the rinse fluid 46 is transferred to the twenty-sixth conduit 74Z which guides the rinse fluid 46 to the portion 22 of the instrument 12 that is engaged with the lid 16 of the chamber 14. A first diverter switch 110A enables the diverter valve 38 to send fluid to either the fluid outlets 24 or to the portion 22 of the instrument 12 that is engaged with the chamber 14. Thus, the rinse fluid 46 is transferred to the chamber 14 due to forces provided by the first pump 72A, the first air valve 76A, the second air valve 76B, and the fourth air valve 76D.

The first and second diverter switches 110A, 110B are preferably integral with their respective air valves and can be controlled by the controller 92. However, those of ordinary skill in the art will appreciate from this disclosure that the first and second diverter switches can be electrically operated solenoid switches, electric motors or the like.

To transfer the bio-burden removing fluid 48 from a second reservoir 44B to the chamber 14, a second pump 72B drives the bio-burden removing fluid 48 through a fifteenth conduit 74O past a second fluid sensor 106B and past a fifth checkvalve 86E. Then, the bio-burden removing fluid 48 enters the eighteenth conduit 74R and is guided toward the diverter valve 38. Then, second air valve 76B is moved into the second position to guide pressurized air from the third conduit 74C to the tenth conduit 74J to aid in driving the bio-burden removing fluid 48 through the eighteenth conduit 74R to the diverter valve 38. The apparatus 10 preferably uses between about six milliliters and about twelve milliliters of bio-burden removing fluid 48 during the complete sterilization process for one instrument 12. However, those of ordinary skill in the art will appreciate from this disclosure that depending on the size of the apparatus and the type of bio-burden removing fluid 48 used, that the amount of bio-burden removing fluid used can be varied without departing from the scope of the present invention.

Depending upon the position of the diverter valve 38, the bio-burden removing fluid 48 is directed toward either the portion 22 of the instrument 12 that is engaged by the chamber 14 or toward the nozzles 24 contained in the chamber 14. When the diverter valve 38 is in the first position 40, the bio-burden removing fluid 48 enters into the twenty-second conduit 74V and is guided to the twenty-third conduit 74W.

Then, the fourth air valve 76D is moved into the second position 42 causing pressurized air to move from the fifth conduit 74E to the twelfth conduit 74L to aid in driving the bio-burden removing fluid 48 from the twenty-third conduit 74W to the fluid outlets 24 in the chamber 14 for application of the bio-burden removing fluid 48 to the exterior 32 of the instrument 12.

When the diverter valve 38 is in the second position 42, the bio-burden removing fluid 48 is transferred to the twenty-sixth conduit 74Z which guides the bio-burden removing fluid 48 to the portion 22 of the instrument 12 which is engaged by the chamber 14. Thus, the bio-burden removing fluid 48 is transferred from the second reservoir 44B to the chamber 14 by the action of the second pump 72B, the second air valve 76B, and the fourth air valve 76D.

The sterilizing fluid 50 is transferred from the third reservoir 44C to the chamber 14 as follows. The third pump 72C transfers the sterilizing fluid 50 from the third reservoir 44C to a sixteenth conduit 74P and drives the sterilizing fluid 50 through a seventh checkvalve 86G. An exhaust valve 198 is attached to the third reservoir 44C to allow air to enter the third reservoir 44C and to reduce the amount of force that must be generated by the third pump 44C to remove the sterilizing fluid 50 from the third reservoir 44C. Then, the sterilizing fluid 50 is pumped into a third heater 86C, through an eighth chechvalve 86H, and into a fourth heater 88D. Once the Sterilizing solution has filled both the third and fourth heaters 88C, 88D, a third fluid sensor 106C indicates that a complete charge of the sterilizing fluid 50 is ready for application after being heated to the predetermined fluid temperature. The sterilizing fluid 50 is preferably applied two times during the sterilization of the instrument 12 (each time providing a full charge of sterilizing fluid 50 to the instrument). The second sterilizing fluid 50 treatment is preferably applied without an intervening rinse fluid 46 application to prevent as much dilution as possible. It is preferred that the total amount of sterilent used by the apparatus 10 during the sterilization of the instrument 12 be between about six milliliters and about thirty milliliters. However, those of ordinary skill in the art will appreciate from this disclosure that greater or lessor amounts of sterilent can be used without departing from the scope of the present invention.

Then, once the sterilizing fluid 50 that is in the twenty-first conduit 74U (i.e.: in the third and fourth heaters 88C, 88D) has reached the predetermined fluid temperature, the third air valve 76C is moved into the second position 42 causing pressurized air to enter the eleventh conduit 74K. The pressurized air is guided to the air diverter valve 108, which is switched into the second position 42 to guide air into the nineteenth conduit 74S, and through the ninth checkvalve 86I. This causes the pressurized air to drive the sterilizing fluid 50 which is contained above the eighth checkvalve 86H through a tenth checkvalve 86J and into the diverter valve 38. Depending upon the position of the diverter valve 38, the sterilizing fluid 50 is either guided toward the fluid outlets 24 in the chamber 14 or toward the portion 22 of the instrument 12 which is engaged by the chamber 14.

When the diverter valve 38 is in the first position 40, the sterilizing fluid 50 is transferred to the twenty-second conduit 74V and into the twenty-third conduit 74W. Then, the fourth air valve 76D is moved into the second position 42 causing pressurized air to enter the twelfth conduit 74L. This causes pressurized air to pass through the eleventh checkvalve 86K and to drive the sterilizing fluid 50 through the twenty-third conduit 74W into the fluid outlets 24 for application to the exterior 32 of the instrument 12 contained within the chamber 14. Alternatively, when the diverter valve 38 is in the second position 42, the sterilizing fluid 50 is transferred to the twenty-sixth conduit 74Z which guides the sterilizing fluid 50 to the portion 22 of the instrument 12 which is engaged by the lid 16 of the chamber 14.

After the application of the sterilizing fluid 50 which was temporarily positioned above the eighth checkvalve 86H is completed, the air diverter valve 108 is moved into the first position 40 causing pressurized air to enter the twentieth conduit 74T and to pass through the sixth checkvalve 86F. This results in the pressurized air driving the remaining sterilizing fluid 50 that is present on the right side of the seventh checkvalve 86G toward the diverter valve 38. Once the remaining sterilizing fluid 50 reaches the diverter valve 38, the sterilizing fluid 50 is guided toward either the fluid outlets 24 in the chamber 14 or toward the portion 22 of the instrument 12 which is engaged with the lid 16 of the chamber 14, as described above.

The chamber 14 further includes at least another fluid outlet 26 to direct the flow of the fluid onto the portion 22 of the instrument 12 engaged by the chamber 14. Accordingly, as described above, fluid is guided through the twenty-sixth conduit 74Z, the fluid is directed towards the portion 22 of the instrument 12 by the other fluid outlet 26. When the instrument 12 has an interior 28 that has a fluid pathway connection to the portion 22 of the instrument 12 engaged by the chamber 14, the other fluid outlet 26 also directs a flow of the fluid into an interior 28 of the instrument 12. As the apparatus 10 of the present invention is preferably used with dental handpieces, the interior 28 of the instrument 12 is sterilized by the application of the sterilizing fluid 50 to the inside of the lumens 124A, 124B. However, those of skill in the art will appreciate from the present invention that the sterilizing apparatus 10 may be used with an instrument 12 not having an interior 28 without departing from the scope of the present invention.

The fluid injection mechanism 20 alternatingly supplies a flow of the fluid to either the one fluid outlet 24 or into the other fluid outlet 26. As detailed above, the fluid injection mechanism 20 includes a diverter valve 38 for alternately supplying a flow of the fluid to the one fluid outlet 24 and to the other fluid outlet 26. While the preferred embodiment of the present invention preferably alternately directs a flow of fluid to either the portion 22 of the instrument 12 engaged by the chamber 14 or to the nozzles 24 of the chamber 14, those of skill in the art will appreciate from this disclosure that the fluid can be supplied simultaneously to both the nozzles 24 and to the portion 22 of the instrument 12 that is engaged by the chamber 14 without departing from the scope of the present invention. For example, the diverter valve 38 can be replaced by a flow divider (not shown) or the like, to simultaneously apply the fluid to both the exterior 32 of the instrument 12 and to the portion 22 of the instrument 12 that is engaged by the chamber 14.

Referring to FIG. 1, the apparatus 10 further includes a drain 52 for removing fluid from the chamber 14, and a drain valve 54 for opening and closing the drain 52. The drain valve 54 is biased into a closed position 56 by a drain valve-biasing element 60. When the drain valve 54 is in the closed position, the fluid is prevented from exiting the chamber 14 by a twelfth checkvalve 86L. A drain switch 68 is capable of moving the drain valve 54 into an open position 58 which allows the fluid to drain from the chamber 14 into a twenty-fourth conduit 74X, which forms a waste line 70.

To facilitate draining fluid from the chamber 14, the drain air valve 64 creates a vacuum to pull the fluid out of the twenty-fourth conduit 74X. More specifically, the drain air valve 64 is shown in FIG. 1 in the first position 40. The drain air valve 64 is biased into the first position 40 by a drain air valve biasing element 82. While the drain air valve 64 is in the first position 40, pressurized air in the thirteenth conduit 74M is transported to the exhaust valve 188 via the eighth conduit 74H.

A drain switch 84 is capable of moving the drain air valve 64 into the second position 42 which allows the drain air valve 64 to supply pressurized air to drive the fluid along the waste line 70 and through a drain nozzle 62, which is attached along the waste line 70. When the drain air valve 64 is in the second position, pressurized air from the sixth conduit 74F is provided to the thirteenth conduit 74M, through the restrictor 190, through the thirteenth checkvalve 86M, and into the waste line nozzle 62.

The airflow through the thirteenth conduit 74M creates a suction effect that pulls the fluid from the twenty-fourth conduit 74X and drives the fluid into a twenty-fifth conduit 74Y. Then, by opening the automatic discharge valves 102 a predetermined amount, air is propelled through the seventh conduit 74G and past the fourteenth checkvalve 86N. The flow of air through the seventh conduit 74G creates a further suction effect to pull the fluid from the twenty-fifth conduit 74Y to a waste line outlet 66 through which the fluid is expelled from the apparatus 10.

A method of sterilizing the instrument 12, which has an exterior surface 32 at substantially room temperature, preferably involves attaching the instrument 12 to the partially porous coupler 30 prior to attaching the instrument 12 to the chamber 14 via the coupler 30. The porous body 34 of the partially porous coupler 30 is preferably formed of a sponge like material having micro-sized pores. A preferred type of sponge-like material is a porous polyethylene material. The method of the present invention preferably, but not necessarily, also includes the steps of determining via a first sensor 36A whether the chamber 14 is closed and determining via a second sensor 36B whether an instrument 12 is enclosed in the chamber 14 prior to beginning the removing of bio-burden.

Afterwards, the instrument is preferably secured inside of the chamber 14 by removably engaging a portion 22 of the instrument 12 to the chamber 14. After an instrument 12 is placed within the chamber 14, bio-burden is removed from the instrument 12 by exposing the instrument 12 to at least one bio-burden removing fluid 48 while maintaining the chamber 14 and the at least one bio-burden removing fluid 48 at about a first predetermined temperature.

The removing of bio-burden includes using a protease fluid to wash the exterior surface 32 of the instrument 12 and to wash the portion 22 of the instrument 12 secured to the chamber 14. When using the apparatus 10 with a dental handpiece, or another instrument 12 having an interior which has a fluid pathway connection to the portion 22 of the instrument 12 that is engaged with the chamber 14, the step of removing bio-burden preferably includes using the protease fluid to wash an interior 28 of the instrument 12 and to wash the portion of the instrument 12 secured to the chamber 14.

Additionally, when using a dental handpiece, or other instrument 12 having an interior connected by a fluid pathway to the portion 22 of the instrument 12 engaged by the chamber, it is preferred, but not necessary, that the step of removing bio-burden includes using a rinse fluid 46 to wash an interior surface 28 of the instrument 12.

The step of removing bio-burden preferably includes using the rinse fluid 46 after using the protease fluid to rinse the exterior surface 32 of the instrument 12 and to rinse the portion 22 of the instrument 12 secured to the chamber 14. Furthermore, the step of removing bio-burden includes alternately driving the at least one bio-burden removing fluid 48 against the exterior surface 32 of the instrument 12 and against a portion 22 of the instrument 12 engaged by the chamber 14.

The method also includes the step of sterilizing the instrument 12, including the portion 22 of the instrument 12 engaged by the chamber 14, by exposing the instrument 12 to at least one sterilizing fluid 50 while maintaining the chamber 14 and the at least one sterilizing fluid 50 at about a second predetermined temperature. Preferably, the first predetermined temperature and the second predetermined temperature are within the range of between about fifty-five degrees Fahrenheit and about ninety-five degrees Fahrenheit. More preferably, the first predetermined temperature and the second predetermined temperature are maintained within the range of about ninety degrees Fahrenheit and about ninety-four degrees Fahrenheit. The sterilizing of the instrument 12 preferably includes using the at least one sterilizing fluid 50 which comprises a peracetic acid to sterilize the exterior surface 32 of the instrument 12 and to sterilize the portion 22 of the instrument 12 secured to the chamber 14. When using the method of the present invention with a dental handpiece, or other instrument 12 having an interior having a fluid pathway to the portion 22, the step of sterilizing the instrument 12 preferably includes using the at least one sterilizing fluid 50 to sterilize an interior 28 of the instrument 12.

Additionally, the step of sterilizing the instrument 12 includes exposing the instrument 12 to the at least one sterilizing fluid 50 for a predetermined period of time. The predetermined period time is preferably between about three minutes and about five minutes. While it is preferred that the predetermined period of time be between about three minutes and about five minutes, those of skill in the art will appreciate from this disclosure that the period of time can be varied depending upon the particular sterilizing fluid 50 being used by the apparatus 10 to sterilize the instrument 12. Additionally, the predetermined period of time can also vary depending upon the specific concentration of the sterilizing fluid 50 which is used.

The method of sterilizing the instrument 12 preferably includes the following steps: applying the at least one sterilizing fluid 50 which comprises a peracetic acid to sterilize the exterior surface 32 of the instrument 12 and to sterilize the portion 22 of the instrument secured to the chamber; exposing the instrument 12 to the at least one sterilizing fluid 50 for a predetermined period of time; removing the at least one sterilizing fluid 50 from the chamber 14; and repeating the above steps of applying the fluid and then exposing the instrument 12.

Additionally, it is preferable to drain the at least one sterilizing fluid 50 from the chamber 14 after the step of sterilizing the instrument 12. The step of sterilizing the instrument 12 preferably includes alternately driving the at least one sterilizing fluid 50 against the exterior surface 32 of the instrument 12 and against the portion 22 of the instrument 12 engaged by the chamber 14.

In operation, the apparatus for sterilizing an instrument is preferably used as follows. Referring the FIGS. 2a–2d, a portion 22 of the instrument 12 is inserted into a porous coupler 30. The porous coupler 30 has an interior porous body 34 with shaped grooves and recesses 116A, 126, 130 for receiving the portion 22 of the instrument 12. When the instrument 12 is a dental handpiece, the lumens 124A, 124B are inserted into lumen receivers 126 and the large lumens 128A, 128B are inserted into large lumen receivers 130.

Referring to FIGS. 3 and 4, the handpiece 12 is directly slid into the porous coupler 30 and preferably maintained therein by at least a friction fit between the portion 22 of the instrument 12 and the porous body 34 of the coupler 30. Then, the porous coupler 30 and the attached handpiece 12 are slid directly into the coupler housing 144, which is part of the lid 16 of the chamber 14. Referring to FIGS. 6 and 7, the porous coupler 30 is gripped by clips 150 which are located within the coupler housing 144.

Referring to FIG. 5, with the handpiece 12 secured to the lid 16 of the chamber 14, the combination of the lid 16 and the handpiece 12 are inserted into the chamber 14. Referring to FIG. 1, once the lid 16 is secured to the chamber 14, a first sensor 36A sends a lid-closed-signal to the controller 92. Then, a second sensor 36B determines whether an instrument 12 is positioned within the chamber 14. If the second sensor 36B detects an instrument 12 within the chamber 14, an instrument-presence-signal is sent to a controller 92. A third sensor 36C is then used to detect a compartment temperature and sends a temperature-signal to the controller 92. If the interior compartment 18 is not generally at the predetermined compartment temperature, then the controller 92 adjusts the heater 90 which surrounds the chamber 14 until the interior compartment 18 is generally at the predetermined compartment temperature.

Next, the controller 92 activates the first pump 72A to drive the rinse fluid 46 from the first reservoir 44A through the fourteenth conduit 74N, through the second checkvalve 86B, and into the second heater 88B until the first fluid detector 106A detects that the appropriate amount of the rinse fluid 46 is present in the seventeenth conduit 74Q.

Then, the first pump 72A preferably terminates pumping the rinse fluid 46 while the second heater 88B, if necessary, brings the rinse fluid 46 up to the predetermined fluid temperature. Once the rinse fluid 46 is generally at the predetermined fluid temperature, the controller 92 causes the first input valve switch 80A to move the first air valve 76A into the second position 42 causing pressurized air to flow from the second conduit 74B to the ninth conduit 74I, through the first checkvalve 86A, and to push the charge of rinse fluid 46 in the second heater 88B past the fourth checkvalve 86D and into the eighteenth conduit 74R.

Then, the controller 92 causes the second input valve switch 80B to move the second air valve 76B into the second position 42 causing pressurized air to flow from the third conduit 74C into the tenth conduit 74J, through the third checkvalve 86C, and to combine with the pressurized air supplied by the first air valve 76A to push the rinse fluid 46 through the diverter valve 38 and into the chamber 14. As detailed above, the diverter valve 38 alternatingly sends a flow of the rinse fluid 46 to either the nozzles 24 in the chamber 14 or the other outlet 26 in the lid 16 of the chamber 14. As detailed above, when the diverter valve 38 sends fluid to the nozzles 24, the fourth air valve 76D is also used to supply pressurized air.

The first application of the rinse fluid 46 to the instrument 12 serves as a pre-wash for the instrument 12. While the rinse fluid 46 is being applied to the handpiece 12, the drain 52 is preferably closed by the drain valve 54. Once the application of the rinse fluid 46 to the exterior of the instrument 12 and to the portion 22 of the instrument 12 engaged by the chamber 14 (and to any interior 28 of the handpiece 12 which is connected by a fluid pathway connection to the portion 22 of the handpiece 12 engaged by the chamber 14) is complete, the drain 52 is opened.

To open the drain 52, the controller 92 activates the drain switch 68 which moves the drain valve 54 into the open position 58 while generally simultaneously activating the drain air valve 64. When the controller 92 activates the drain air valve 64, the drain air valve switch 84 moves the drain air valve 64 into the second position 42 causing pressurized air to flow from the sixth conduit 74F into the thirteenth conduit 74M, through the restrictor 190, through the thirteenth checkvalve 86M, and into the twenty-fifth conduit 74Y.

The flow of the pressurized air from the thirteenth conduit 74M into the twenty-fifth conduit 74Y creates a suction affect causing the rinse fluid 46 which is present in the chamber 14 to be drawn into the twenty-fourth conduit 74X. Then, the controller 92 causes the automatic discharge 102 to open and sends pressurized air into the seventh conduit 74G, through the fourteenth checkvalve 86N, and into the twenty-fifth conduit 74Y. The flow of pressurized air from the seventh conduit 74G into the twenty-fifth conduit 74Y creates a vacuum affect which further draws the remaining rinse fluid 46 from the chamber 14 and through the waste line outlet 66.

While the rinse fluid 46 is being removed from the chamber 14, a partial drying phase is preferably, but not necessarily, initiated. The controller 92 moves the second and fourth air valves 76B, 76D into the second position 42 causing pressurized air to be guided toward the fluid outlets 24 in the chamber 14 sides and to the other fluid outlet 26. The application of pressurized air to the instrument 12 does not "dry" the instrument 12, but the pressurized air does remove the larger water droplets from the instrument 12.

Once the rinse fluid 46 has been removed from the chamber 14 and the partial drying phase is complete, the controller 92 deactivates the drain switch 68 causing the drain biasing element 60 to move the drain valve 54 into the closed position 56. It is then preferable that the controller 92 deactivates the first air valve 76A, the second air valve 76B, the drain air valve 64, and the automatic discharge 102 in preparation for treating the instrument 12 with the next fluid as detailed below. However, those of skill in the art will appreciate from this disclosure that the above-mentioned valves and the auto-discharge 102 can be closed at another point in the process without departing from the scope of the present invention as long as the proper transfer of the rinse fluid 46 is not interrupted.

After the above-described application of the rinse fluid 46 to the instrument 12, the apparatus uses the bio-burden removing fluid 48 to clean the instrument 12 as follows. The second pump 72B drives the bio-burden removing fluid 48 into the fifteenth conduit 74O until the second fluid sensor 106B determines that the appropriate amount of bio-burden removing fluid 48 is present in the fifteenth conduit 74O. Then, the bio-burden removing fluid is pumped past the fifth checkvalve 86E and into the eighteenth conduit 74R. The controller 92 then activates the second air valve 76B by causing the second input valve switch 80B to move the second air valve 76B into the second position 42. This causes pressurized air to be guided from the third conduit 74C into the tenth conduit 74J, to be guided past the third checkvalve 86C, and to drive the bio-burden removing fluid 48 from the eighteenth conduit 74R to the diverter valve 38.

As described above, the diverter valve 38 causes the bio-burden removing fluid 48 to be guided to either the nozzles 24 in the chamber 14 or to the coupler 30 which secures the instrument 12 to the chamber 14. After the bio-burden removing fluid 48 has been applied to the instrument 12, the fluid is preferably left in contact with the instrument 12 for about one minute to about ten minutes (more preferably for about one minute to about five minutes). Then, a second application of the bio-burden removing fluid 48 is preferably applied to the instrument 12 and left in contact with the instrument as detailed above. Thus, the total contact time of the bio-burden removing fluid 48 with the instrument 12 for two applications of the bio-burden removing fluid 48 is preferably, but not necessarily, about two minutes to about 20 minutes (more preferably for about two minutes to about ten minutes)

After the second application of the bio-burden removing fluid 48 has been in contact with the handpiece 12 for the preferred period of time, the controller 92 activates the drain switch 68 to cause the drain valve 54 to move into the open position 58. Then, the controller 92 uses the drain air valve 64 and the auto-discharge 102 to remove the bio-burden removing fluid 48 from the chamber 14 in the manner described above.

After the completion of the treating of the instrument 12 with the bio-burden removing fluid 48, it is preferable to use the rinse fluid 46 to remove any remaining bio-burden removing fluid 48 from the instrument 12. Thus, the controller 92 causes the apparatus 10 to again apply the rinse fluid 46 to the instrument 12 in the manner described above. After the rinse fluid 46 has been applied to the instrument, a second partial dry phase is preferably performed in the same manner as detailed above.

Once the bio-burden has been removed from the instrument 12 and the partial dry phase has been completed, the pathogens, which are present on the instrument 12, are exposed to facilitate a total kill of the pathogens using the sterilizing fluid 50. To apply the sterilizing fluid 50 to the handpiece 12, the apparatus 10 operates as follows. The controller 92 activates the third pump 72C to drive the sterilizing fluid 50 into the sixteenth conduit 74P, through the seventh checkvalve 86G, and into the twenty-first conduit 74U until the third and fourth heaters 88C, 88D are filled with the sterilizing fluid 50 and the third fluid sensor 106C indicates a full charge of the sterilizing fluid 50 is present in the twenty-first conduit 74U.

Then, the controller 92 activates the third input valve switch 80C to move the third air valve 76C into the second position 42 causing pressurized air to flow from the fourth conduit 74D into the eleventh conduit 74K. At approximately the same time, the controller 92 uses the second diverter switch 110B to move the air diverter valve 108 into the second position 42 causing the pressurized air in the eleventh conduit 74K to push the sterilizing fluid 50 that is positioned above the eighth checkvalve 86H to the diverter valve 38. Then, the diverter valve 38 guides the sterilizing fluid 50 toward the chamber 14 as described above.

Once the sterilizing fluid 50 that is positioned above the eighth checkvalve 86H has been applied to the instrument 12, the controller 92 uses the second diverter switch 110B to move the air diverter valve 108 into the first position 40 causing the pressurized air in the eleventh conduit 74K to drive the remaining sterilizing fluid 50 which is present in the twenty-first conduit 74U to the diverter valve 38. Then, the remaining sterilizing fluid 50 is applied to the handpiece 12.

Once the sterilizing fluid 50 has been applied to the handpiece 12, it is preferable that the drain 52 remain closed and that the instrument 12 remain exposed to the sterilizing fluid for a predetermined period of time. As discussed above, it is preferable that the instrument 12 be exposed to the sterilizing fluid 50 for a period of time between about three minutes and about seven minutes (more preferably between about three minutes and about four and one half minutes). Once the instrument 12 has been exposed to the sterilizing fluid 50 for the predetermined period of time, the sterilizing fluid 50 is removed from the chamber 14 in a manner similar to that described above with reference to the rinse fluid 46.

Once the application of the sterilizing fluid 50 is complete, it is preferable to again expose the instrument 12 to a second application of the sterilizing fluid 50. Once the second application of the sterilizing fluid 50 is complete and the instrument 12 has been left in contact with the second application of the sterilizing fluid 50 for a predetermined period of time, the instrument 12 is again rinsed using the rinse fluid 46. After the final application of the rinse fluid 46, another partial drying phase is preferably performed and the instrument 12 sterilization process is complete.

It is recognized by those skilled in the art, that changes may be made to the above-described embodiment of the present invention without departing from the broad inventive concept thereof. It is understood, therefor, that this invention is not limited to the particular embodiment disclosed, but is intended to cover all modifications which are within the spirit and scope of the invention as defined by the appended claims.

We claim:

1. An apparatus for sterilizing an instrument having an exterior surface, the apparatus comprising:

a chamber having an interior compartment, a chamber heater and an interior compartment temperature sensor, the chamber configured to releasably secure the instrument in the interior compartment, the chamber heater in thermal communication with the interior compartment, the interior compartment temperature sensor in thermal communication with the interior compartment;

at least one fluid outlet in the interior compartment, the at least one fluid outlet configured to apply sterilizing fluid onto the exterior surface of the instrument;

a fluid injection mechanism having a fluid heater and a fluid temperature sensor, the fluid injection mechanism in fluid communication with the at least one fluid outlet, the fluid heater in thermal communication with the fluid injection mechanism, the fluid temperature sensor in thermal communication with the fluid; and a controller in electrical communication with the interior compartment temperature sensor, the fluid temperature sensor, the chamber heater and the fluid heater, the controller configured to operate in at least a first mode, wherein the temperature of the fluid and the temperature of the interior compartment ate maintained at about a predetermined temperature based on the sterilizing fluid.

2. The apparatus of claim 1, wherein the controller is configured to operate in a plurality of modes comprising the first mode and a second mode wherein the temperature of the fluid and the temperature of the interior compartment are maintained within a range of between about fifty-five degrees Fahrenheit and about ninety-five degrees Fahrenheit.

3. The apparatus of claim 1, wherein the controller is configured to operate in a plurality of modes comprising the first mode, the second mode and a third mode wherein the temperature of the fluid and the temperature of the interior compartment are maintained within a range of between about ninety degrees Fahrenheit and about ninety-four degrees Fahrenheit.

4. The apparatus of claim 1, wherein the at least one fluid outlet comprises at least one nozzle mounted to the chamber to direct a flow of the fluid onto the exterior surface of the instrument.

5. The apparatus of claim 1, further comprising:

a first sensor for detecting when the chamber is closed; and a second sensor for detecting when the instrument is positioned within the interior compartment, the first and second sensors in electrical communication with the controller.

6. The apparatus of claim 1, wherein the instrument has an interior and the apparatus further comprises at least another outlet to direct a flow of the fluid into the interior of the instrument and the fluid injection mechanism alternatingly supplies a flow of the fluid to the at least one fluid outlet and to the other fluid outlet.

7. The apparatus of claim 6, further comprising a diverter valve for alternately supplying a flow of the fluid to the at least one fluid outlet and to the other fluid outlet.

8. The apparatus of claim of claim 1, further comprising a drain for removing the fluid from the chamber.

9. The apparatus of claim 8, further comprising:
a drain valve for opening and closing the drain;
a waste line connected to the drain;
a drain nozzle attached along the waste line;
a drain air valve capable of supplying air to drive the fluid along the waste line and through the drain nozzle; and
a waste line outlet through which fluid is expelled from the apparatus.

10. The apparatus of claim 1, wherein the fluid injection mechanism comprises:
a reservoir for storing the fluid;
a conduit extending between the reservoir and the chamber; and
a pump for removing fluid from the reservoir and driving the fluid through the conduit toward the chamber.

11. The apparatus of claim 10, further comprising an air valve attached to the fluid injection mechanism for supplying pressurized air to remove fluid from the conduit.

12. A method of sterilizing an instrument at substantially room temperature while only exposing the instrument to substantially room temperatures, the instrument having an exterior surface, the method comprising the steps of:
securing the instrument inside of a chamber by removably engaging a portion of the instrument to the chamber;
removing bio-burden by washing an interior and the entire exterior surface of the instrument using a rinse fluid;
further removing bio-burden from the instrument by exposing the interior and the entire exterior surface of the instrument to at least a protease fluid while maintaining the chamber and the at least one protease fluid at about a first predetermined, substantially room temperature; and
sterilizing the interior and the entire exterior surface of the instrument by exposing the instrument to at least one peracetic acid fluid while maintaining the chamber and the at least one peracetic acid at about a second predetermined, substantially room temperature.

13. The method of claim 12, wherein the first predetermined, substantially room temperature and the second predetermined substantially room temperature are within the range of between about fifty-five degrees Fahrenheit and about ninety-five degrees Fahrenheit.

14. The method of claim 13, wherein the first predetermined, substantially room temperature and the second predetermined substantially room temperature are maintained within the range of about ninety degrees Fahrenheit and about ninety-four degrees Fahrenheit.

15. The method of claim 12, wherein the step of sterilizing the instrument includes exposing the instrument to the at least one sterilizing fluid for a predetermined period of time.

16. The method of claim 15, wherein the predetermined period of time is between about three minutes and about five minutes.

17. The method of claim 16
exposing the instrument to the at least one sterilizing fluid for a predetermined period of time;
repeating the above step of exposing the instrument; and
removing the at least one sterilizing fluid from the chamber;
wherein each of the steps of the method of sterilizing an instrument is repeated except for the step of securing the instrument.

18. The method of claim 17, further comprising the step of draining the at least one sterilizing fluid from the chamber after the step of sterilizing the instrument.

19. The method of claim 12, further comprising the steps of:
determining via a first sensor whether the chamber is closed; and
determining via a second sensor whether the instrument is enclosed in the chamber prior to beginning the removing of bio-burden.

20. The method of claim 12, wherein the step of removing bio-burden includes repeatedly alternately driving the at least one protease fluid against the entire exterior surface of the instrument and into the interior of the instrument.

21. The method of claim 12, wherein the step of sterilizing the instrument includes repeatedly alternately driving the at least one peracetic acid fluid against the exterior surface of the instrument and into the interior of the instrument.

22. An apparatus for sterilizing a dental handpiece while only exposing the dental handpiece to substantially room temperatures, the dental handpiece having an exterior surface, the apparatus comprising:
a chamber having an interior compartment for receiving and housing the dental handpiece, the interior compartment being maintained at a predetermined, substantially room temperature, compartment temperature while the dental handpiece is being sterilized, the chamber being releasably engagable with a portion of the dental handpiece to support the dental handpiece within the interior compartment;
a fluid injection mechanism in fluid communication with the chamber for supplying fluid to the chamber and for maintaining the fluid at a predetermined, substantially room temperature, fluid temperature while the dental handpiece is being sterilized;
the chamber including at least one fluid outlet disposed in the interior compartment in a spaced apart fashion from the dental handpiece to convert a flow of the fluid into a mist spray that contacts the exterior surface of the dental handpiece and at least another fluid outlet to direct a flow of the fluid into an interior the dental handpiece, the at least one fluid outlet comprising at least one nozzle mounted to the chamber to direct a flow of the fluid onto the exterior surface of the dental handpiece, each at least one nozzle comprising:
a first spacer for receiving a fluid from the fluid injection mechanism;
a first nozzle plate having a first and second surface, the first surface being disposed on a distal end of the first spacer and having at least one hole therein;
second spacer disposed on the second surface of the first nozzle plate; and
a second nozzle plate attached on an opposite end of the second spacer from the first nozzle plate and having a hole therein; and wherein the apparatus sterilizes the interior and the entire exterior surface of the dental handpiece.

23. A method of sterilizing an instrument at substantially room temperature while only exposing the instrument to substantially room temperatures, the instrument having an exterior surface, the method comprising the steps of:

securing the instrument inside of a chamber by removably engaging a portion of the instrument to the chamber; then removing bio-burden by washing an interior and the entire exterior surface of the instrument using a rinse fluid; then further removing bio-burden from the instrument by exposing the interior and the entire exterior surface of the instrument to at least a protease fluid while maintaining the chamber and the protease fluid at about a first predetermined, substantially room temperature; and then sterilizing the interior and the entire exterior surface of the instrument by exposing the instrument to at least one peracetic acid fluid while maintaining the chamber and the at least one peracetic acid fluid at about a second predetermined, substantially room temperature.

24. An apparatus for sterilizing an instrument while only exposing the instrument to substantially room temperatures, the instrument having an exterior surface, the apparatus comprising:

a chamber having an interior compartment for receiving and housing the instrument, the interior compartment being maintained at a predetermined, substantially room temperature, compartment temperature while the instrument is being sterilized, the chamber being releasably engagable with a portion of the instrument to support the instrument within the interior compartment;

a fluid injection mechanism in fluid communication with the chamber for supplying fluid to the chamber and for maintaining the fluid at a predetermined, substantially room temperature, fluid temperature while the instrument is being sterilized;

the chamber including at least one nozzle disposed in the interior compartment in a spaced apart fashion from the instrument for converting a flow of the fluid into a mist spray that contacts the exterior surface of the instrument, each at least one nozzle comprising:

a first spacer for receiving a fluid from the fluid injection mechanism;

a first nozzle plate having a first and second surface, the first surface being disposed on a distal end of the first spacer and having at least one hole therein;

a second spacer disposed on the second surface of the first nozzle plate; and a second nozzle plate attached on an opposite end of the second spacer from the first nozzle plate and having a hole therein; the chamber further including at least another fluid outlet to direct a flow of the fluid into an interior the instrument; and wherein the apparatus sterilizes the interior and the entire exterior surface of the instrument.

25. An apparatus for sterilizing an instrument while only exposing the instrument to substantially room temperatures, the instrument having an exterior surface, the apparatus comprising:

a chamber having an exterior chamber surface and an interior compartment for receiving and housing the instrument, the interior compartment being maintained at a predetermined, substantially room temperature, compartment temperature while the instrument is being sterilized, the chamber being releasably engagable with a portion of the instrument to support the instrument within the interior compartment;

a fluid injection mechanism in fluid communication with the chamber for supplying fluid to the chamber and for maintaining the fluid at a predetermined, substantially room temperature, fluid temperature while the instrument is being sterilized;

the chamber including at least one nozzle disposed in the interior compartment in a spaced apart fashion from the dental handpiece for converting a flow of the fluid into a mist spray that contacts the exterior surface of the instrument, each at least one nozzle being releasably engagable with and inserted into the exterior chamber surface of the chamber to establish a fluid pathway into the interior compartment;

the chamber further including at least another fluid outlet to direct a flow of the fluid into an interior the instrument; and wherein the apparatus sterilizes the interior and the entire exterior surface of the instrument.

* * * * *